United States Patent [19]
Krieger et al.

[11] Patent Number: 5,510,466
[45] Date of Patent: Apr. 23, 1996

[54] SCAVENGER RECEPTOR PROTEIN AND ANTIBODY THERETO

[75] Inventors: Monty Krieger, Needham; Tatsuhiko Kodama, Waban, both of Mass.

[73] Assignee: Massachusetts Institute of Technology, Cambridge, Mass.

[21] Appl. No.: 307,400

[22] Filed: Sep. 16, 1994

Related U.S. Application Data

[63] Continuation of Ser. No. 997,113, Dec. 24, 1992, abandoned, which is a continuation of Ser. No. 391,486, Aug. 9, 1989, abandoned, which is a continuation-in-part of Ser. No. 272,002, Nov. 15, 1988, abandoned.

[51] Int. Cl.$^6$ .......................... C07H 21/04; C07K 14/47; C07K 14/705; C07K 17/00
[52] U.S. Cl. .......................... 530/395; 530/350; 530/810; 536/23.5
[58] Field of Search ...................... 436/71, 503; 935/11; 530/350, 356, 395, 402, 810, 811, 812; 536/23.5

[56] References Cited

U.S. PATENT DOCUMENTS

| | | | |
|---|---|---|---|
| 4,359,453 | 11/1982 | Gordon | 424/1 |
| 4,451,570 | 5/1984 | Royston et al. | 435/240 |
| 4,529,694 | 7/1985 | Lazarus et al. | 435/68 |
| 4,577,636 | 3/1986 | Spears | 128/654 |
| 4,647,445 | 3/1987 | Lees | 424/1.1 |
| 4,660,563 | 4/1987 | Lees | 128/654 |
| 5,192,507 | 3/1993 | Taylor et al. | 422/68.1 |

FOREIGN PATENT DOCUMENTS

| | | |
|---|---|---|
| 0163041 | 12/1985 | European Pat. Off. . |
| 0189688 | 8/1986 | European Pat. Off. . |

OTHER PUBLICATIONS

*FASEB Journal*, vol. 6, No. 1, Jan. 1, 1992, Abstracts Nos. 2135 and 2137.
Takahashi et al, Abstracts of Ninth Int. Symp. on Atherosclerosis, Rosemont, IL. Oct. 6–11, 1991, p. 133, Abstract No. 148.
Ottnad et al, *Abstracts of Ninth Int. Symp. on Atherosclerosis*, Rosemont, IL, Oct. 6–11, 1991, p. 210, Abs. No. 205.
Creighton, *Proteins*, W. H. Freeman and Co. 1984, p. 67.
Hostikka et al, "Nucleotide Sequence Coding for the Human Type IV Collagen $\alpha_2$ cDNA . . . ", FEBs Letters, vol. 216, No. 2, Jun. 1987, pp. 281–286.
Kolata, New York Times, Oct. 25, 1988, Section C–1 "New Theory Explains How Cholesterol Threatens The Heart".
Hara et al. (1987) Biochemical and Biophysical Research Communications, 146:802–808.
Pitas et al. (1985) The Journal of Cell Biology, 100:103–117.
Dresel et al. (1985) The EMBO Journal, 4:1157–1162.
Via et al. (1985) The Journal of Biological Chemistry, 260:7379–7386.
Dresel et al. (1984) Agents Actions (Suppl.), 16:153–61 (Abstract).
Wong et al. (1983) Arteriosclerosis Abstracts, 3:(5) 475a–476a.
Steinbrecher et al. (1984) Proc. Natl. Acad. Sci. USA, 81:3883–3887.

(List continued on next page.)

Primary Examiner—Jeffrey E. Russel
Attorney, Agent, or Firm—Arnall Golden & Gregory

[57] ABSTRACT

A substantially pure receptor protein capable of binding acetylated low density lipoprotein and oxidized low density lipoprotein is disclosed herein. This protein is characterized by having a molecular weight of about 220,000 daltons, and an affinity for oxidized low density lipoprotein and acetylated low density lipoprotein. Further, it is an integral membrane protein which includes a collagen domain. Proteins having an affinity for the receptor protein as well as DNA sequences encoding at least a portion of the receptor protein are also disclosed herein. In addition, devices for purification purposes and methods for detecting atherosclerotic plaques are described, both of which utilize the receptor protein or binding proteins thereto.

17 Claims, 16 Drawing Sheets

OTHER PUBLICATIONS

Kingsley et al. (1984) Proc. Natl. Acad. Sci. USA, 81:5454–5458.
Nagelkerke et al. (1983) The Journal of Biological Chemistry, 258:12221–12227.
van Der Schroeff et al. (1983) Experimental Cell Research, 145:95–103.
Brown et al. (1983) Ann. Review Biochem., 52:223–261.
Krieger (1983) Cell, 33:413–422.
Via et al. (1982) Circulation, 66:II–37 Abstract No. 148.
Lees and Myers (1982) Adv. Int. Med., 27:475–509.
Brown et al. (1980) Journal of Supramolecular Structure, 13:67–81.
Brown et al. (1979) J. Cell Biology 82:597–613.
Knaw et al. (1982) J. Nuclear Medicine, 23:1011–1019.
Scearce and Eisenbarth (1983) *Methods in Enzymology*, "Production of Monoclonal Antibodies Reacting with Cytoplasm and Surface of Differentiated Cells", 103:459–469.
Oi et al. (1980) *Selected Methods in Cellular Immunology*, pp. 351–372.
Zurawski et al. (1980) *Monoclonal Antibodies . . .* , pp. 19–20.
Shulman et al. (1978) Nature, 276:269–270.
Kohler et al. (1976) Eur. J. Immunol., 6:511–519.
Hnatowich et al. (1973) Science, 220:613–615.
Meares et al. (1984) Analytical Biochemistry, 142:68–78.
Roitt (1980) *Essential Immunology*, pp. 137–171.
Schneider et al. (1980) The J. Biol. Chem., 255:11442–11447.
Daniel et al. (1983) Journal of Biological Chemistry, 7:4606–4611.
Laemmli (1970) Nature, 227:680–685.
Beisiegel et al. (1981) The Journal of Biological Chemistry, 256:(22) 11923–11931.
Tsang et al. (1983) Methods in Enzymology, 92:377–391.
Elder et al. (1982) Proc. Natl. Acad. Sci. USA, 79:4540–4544.
Kozarsky et al. (1986) The Journal of Cell Biology, 102:15671575.
Adamson III, et al. (1983) The Journal of Immunology, 130:(1) 204–208.

```
1                                                    50
TAAATCGGTGCTGCCGTCTTTAGGACATATGAAGTATGGCACAGTGGGAT
                                   1           5
                                   M*  A   Q   W   D 51                                                   100
GACTTTCCTGATCAGCAAGAGGACACTGACAGCTGTACAGAGTCTGTGAA
6                                                    22
D   F   P   D   Q   Q   E   D   T   D   S   C   T   E   S   V   K 101                                                  150
GTTCGATGCTCGCTCAGTGACAGCTTTGCTTCCTCCCCATCCTAAAAATG
23                                                   39
 F   D   A   R   S   V   T   A   L   L   P   P   H   P   K   N   G 151                                                  200
GCCCAACTCTTCAAGAGAGGATGAAGTCTTATAAAACTGCACTGATCACC
  40                                                 55
  P   T   L   Q   E   R   M   K   S   Y   K   T   A   L   I   T 201                                                  250
CTTTATCTCATTGTGTTTGTAGTTCTCGTGCCCATCATTGGCATAGTGGC
56                                                   72
L   Y   L   I   V   F   V   V   L   V   P   I   I   G   I   V   A 251                                                  300
AGCTCAGCTCCTGAAATGGGAAACGAAGAATTGCACGGTTGGCTCAGTTA
73                                                   89
 A   Q   L   L   K   W   E   T   K   N   C   T   V   G   S   V   N 301                                                  350
ATGCAGATATATCTCCAAGTCCGGAAGGCAAAGGAAATGGCAGTGAAGAT
 90                                                  105
  A   D   I   S   P   S   P   E   G   K   G   N   G   S   E   D 351                                                  400
GAAATGAGATTTCGAGAAGCTGTGATGGAACGCATGAGCAACATGGAAAG
106                                                  122
E   M   R   F   R   E   A   V   M   E   R   M   S   N   M   E   S 401                                                  450
CAGAATCCAGTATCTTTCAGATAATGAAGCCAATCTCCTAGATGCTAAGA
123                                                  139
 R   I   Q   Y   L   S   D   N   E   A   N   L   L   D   A   K   N
 .   .   .   .   .   .   .   .   .   .   .   .   .   .   .   .   .
```

*FIG. 3A*

```
451                                               500
ATTTCCAAAATTTCAGCATAACAACTGATCAAAGATTTAATGATGTTCTT
140         ___                                   155
  F  Q  N  F  S  I  T  T  D  Q  R  F  N  D  V  L
     .  .

501                                               550
TTCCAGCTAAATTCCTTACTTTCCTCCATCCAGGAACATGAGAATATCAT
156                                               172
  F  Q  L  N  S  L  L  S  S  I  Q  E  H  E  N  I  I 551                                               600
AGGGGATATCTCCAAGTCATTAGTAGGTCTGAACACCACAGTACTTGATT
173                            ___                189
  G  D  I  S  K  S  L  V  G  L  N  T  T  V  L  D  L 601                                               650
TGCAGTTCAGTATTGAAACACTGAATGGCAGAGTCCAAGAGAATGCATTT
190                                               205
  Q  F  S  I  E  T  L  N  G  R  U  Q  E  N  A  F 651                                               700
AAACAACAAGAGGAGATGCGTAAATTAGAGGAGCGTATATACAATGCATC
206                                      _____   222
  K  Q  Q  E  E  M  R  K  L  E  E  R  I  Y  N  A  S 701                                               750
AGCAGAAATTAAGTCTCTAGATGAAAAACAAGTATATTTGGAACAGGAAA
223                                               239
  A  E  I  K  S  L  D  E  K  Q  U  Y  L  E  Q  E  I 751                                               800
TAAAAGGGGAAATGAAACTGTTGAATAATATCACTAATGATCTGAGGCTG
240                   ___                         255
  K  G  E  M  K  L  L  N  N  I  T  N  D  L  R  L
        .  .  .  .    .        .  .  .  .

801                                               850
AAGGATTGGGAACATTCTCAGACATTGAAAAATATCACTTTACTCCAAGG
256                            ___                272
  K  D  W  E  H  S  Q  T  L  K  N  I  T  L  L  Q  G
                                              __ __
  .  .

851                                               900
TCCTCCTGGACCTCCAGGTGAAAAAGGAGATAGAGGCCCTCCTGGACAAA
273                                               289
  P  P  G  P  P  G  E  K  G  D  R  G  P  P  G  Q  N
  __ __ __ __ __ __ __ __ __ __ __ __ __ __ __ __ __
```

*FIG. 3B*

```
901                                               950
ATGGTATACCAGGCTTTCCAGGTCTAATAGGTACTCCAGGTCTTAAAGGT
290                                             305
  G   I   P   G   F   P   G   L   I   G   T   P   G   L   K   G 951                                              1000
GATCGGGGGATCTCTGGTTTACCTGGAGTTCGAGGATTCCCAGGACCAAT
306                                             322
  D   R   G   I   S   G   L   P   G   V   R   G   F   P   G   P   M 1001                                             1050
GGGGAAGACCGGGAAGCCAGGACTTAATGGACAAAAAGGCCAGAAGGGAG
323                                             339
  G   K   T   G   K   P   G   L   N   G   Q   K   G   Q   K   G   E 1051                                             1100
AAAAAGGGAGTGGAAGCATGCAAAGACCAGGATAACTCCCTGATCGTATT
340                       349
  K   G   S   G   S   M   Q   R   P   G   *

1101                                             1150
AGGCAGGCCCCTTTGAAGATCAGGTGGGTTGGGCGGGACACCCCGTGCTA
1151                                             1200
CCATCTCATTAAAAGGCCCTTCATCTCTGGACAAGTCATCAGCCACATCT
1201                                             1250
GACTCCAGGATTCCCTTGTGGCTCCTCCAAACCGACCTTGGTTCCCACGT
1251                                             1300
GGTGTCAGCTACCTGTCCGCTCTCCAGCACCTCTCCATGACCACTGTCCC
1301                                             1350
TGAGCTGGGATGCCTCCATGACTCACTCATCTAGTGTCTCCCGAATCATT
1351                                             1400
GGCTCCCAGGAGAAATTTCATGGTAACAGATTATATGTGAGTTCTTTACC
1401                                             1450
CTCAAACATATCAGTCTCAGCCAGAGATAGTGATGCCATACAGCTAATAA
1451                                             1500
GATAGCTGTTGTCTCTGGCCTTCCAGAACTAATTGTCCCTGAAAAACATA
1501                                             1550
GCCATGGACACAAGCAGTTATGCATTAGAGCAGGGCTAGATGGGGGAAGG
1551                                             1600
AACTGGGCTCCGTGGGTGTTCAGAGGGGATCAAGAGTCTTCAATTCCTTA
1601                                             1650
GAATTTTAAAAGGTAAATTCAAGTTTTGTCATGAAGTCAAGTGGAGCTG
1651                                             1700
GGGCAGTTCCTTCAAAATTTTTTAGCCAAAAAAAAAAAAAATCAAAATTT
1701                                             1750
GTTGCCTTAAATTACCAGGCTCTTTCAAGCAAGAATATTTTGACCATAAA
1751                                             1800
AAAATAATGCTGAAACTATTTTATTCTATAAAGCTCTTTTCACCAGCCCT
1801
CGTGCCG
```

FIG. 3C

```
126                                                     170
AGTATGGCACAGTGGGATGACTTTCCTGATCAGCAAGAGGACACTGACAG
  1                                                      16
   M*  A   Q   W   D   D   F   P   D   Q   Q   E   D   T   D   S 173                                                     220
CTGTACAGAGTCTGTGAAGTTCGATGCTCGCTCAGTGACAGCTTTGCTTC
17                                                      33
   C   T   E   S   V   K   F   D   A   R   S   V   T   A   L   L   P 223                                                     270
CTCCCCATCCTAAAAATGGCCCAACTCTTCAAGAGAGGATGAAGTCTTAT
 34                                                      49
    P   H   P   K   N   G   P   T   L   Q   E   R   M   K   S   Y 273                                                     320
AAAACTGCACTGATCACCCTTTATCTCATTGTGTTTGTAGTTCTCGTGCC
50                                                      66
 K   T   A   L   I   T   L   Y   L   I   V   F   V   V   L   V   P 323                                                     370
CATCATTGGCATAGTGGCAGCTCAGCTCCTGAAATGGGAAACGAAGAATT
67                                                      83
  I   I   G   I   V   A   A   Q   L   L   K   W   E   T   K   N   C 373                                                     420
GCACGGTTGGCTCAGTTAATGCAGATATATCTCCAAGTCCGGAAGGCAAA
84                                                      99
   T   V   G   S   V   N   A   D   I   S   P   S   P   E   G   K 423                                                     470
GGAAATGGCAGTGAAGATGAAATGAGATTTCGAGAAGCTGTGATGGAACG
100                                                     116
 G   N   G   S   E   D   E   M   R   F   R   E   A   V   M   E   R 473                                                     520
CATGAGCAACATGGAAAGCAGAATCCAGTATCTTTCAGATAATGAAGCCA
117                                                     133
  M   S   N   M   E   S   R   I   Q   Y   L   S   D   N   E   A   N 523                                                     570
ATCTCCTAGATGCTAAGAATTTCCAAAATTTCAGCATAACAACTGATCAA
134                                                     149
    L   L   D   A   K   N   F   Q   N   F   S   I   T   T   D   Q
```

*FIG. 4A*

```
573                                                   620
AGATTTAATGATGTTCTTTTCCAGCTAAATTCCTTACTTTCCTCCATCCA
150                                                   166
 R  F  N  D  V  T  F  Q  T  N  S  L  L  S  S  I  Q 623                                                   670
GGAACATGAGAATATCATAGGGGATATCTCCAAGTCATTAGTAGGTCTGA
167                                                   183
  E  H  E  N  I  I  G  D  I  S  K  S  L  V  G  L  N 673                                                   720
ACACCACAGTACTTGATTTGCAGTTCAGTATTGAAACACTGAATGGCAGA
184                                                   199
   T  T  V  L  D  L  Q  F  S  I  E  T  L  N  G  R 723                                                   770
GTCCAAGAGAATGCATTTAAACAACAAGAGGAGATGCGTAAATTAGAGGA
200                                                   216
V  Q  E  N  A  F  K  Q  Q  E  E  M  R  K  L  E  E 773                                                   820
GCGTATATACAATGCATCAGCAGAAATTAAGTCTCTAGATGAAAAACAAG
217                                                   233
  R  I  Y  N  A  S  A  E  I  K  S  L  D  E  K  Q  V 823                                                   870
TATATTTGGAACAGGAAATAAAAGGGGAAATGAAACTGTTGAATAATATC
234                                                   249
   Y  L  E  Q  E  I  K  G  E  M  K  L  L  N  N  I 873                                                   920
ACTAATGATCTGAGGCTGAAGGATTGGGAACATTCTCAGACATTGAAAAA
250                                                   266
T  N  D  L  R  L  K  D  W  E  H  S  Q  T  L  K  N 923                                                   970
TATCACTTTACTCCAAGGTCCTCCTGGACCTCCAGGTGAAAAGGAGATA
267                                                   283
 I  T  L  L  Q  G  P  P  G  P  P  G  E  K  G  D  R 973                                                   1020
GAGGCCCTCCTGGACAAAATGGTATACCAGGCTTTCCAGGTCTAATAGGT
284                                                   299
   G  P  P  G  Q  N  G  I  P  G  F  P  G  L  I  G
```

*FIG. 4B*

```
1023                                           1070
ACTCCAGGTCTTAAAGGTGATCGGGGGATCTCTGGTTTACCTGGAGTTCG
300                                            316
T   P   G   L   K   G   D   R   G   I   S   G   L   P   G   V   R 1073                                           1120
AGGATTCCCAGGACCAATGGGGAAGACCGGGAAGCCAGGACTTAATGGAC
317                                            333
 G   F   P   G   P   M   G   K   T   G   K   P   G   L   N   G   Q 1123                                           1170
AAAAAGGCCAGAAGGGAGAAAAACCCACTCCAACCATCCAAACACAATCT
334                                            349
  K   G   Q   K   G   E   K   G   S   G   S   M   Q   R   Q   S 1173                                           1220
AATACAGTCCGACTGGTGGGTGGCAGCGGCCCTCACGAAGGCAGAGTGGA
350                                            366
N   T   V   R   L   V   G   G   S   G   P   H   E   G   R   V   E 1223                                           1270
GATTTTTCACGAAGGCCAGTGGGGTACGGTGTGTGACGACCGCTGGGAAC
367                                            383
  I   F   H   E   G   Q   W   G   T   V   C   D   D   R   W   E   L 1273                                           1320
TGCGTGGAGGACTGGTCGTCTGCAGGAGCTTGGGATACAAAGGTGTTCAA
384                                            399
   R   G   G   L   V   V   C   R   S   L   G   Y   K   G   V   Q 1323                                           1370
AGTGTGCATAAGCGAGCTTATTTTGGAAAAGGTACGGGTCCAATATGGCT
400                                            416
S   V   H   K   R   A   Y   F   G   K   G   T   G   P   I   W   L 1373                                           1420
GAATGAAGTATTTTGTTTCCCCAAAGAGTCATCCATTGAAGAGTGCAGAA
417                                            433
 N   E   V   F   C   F   G   K   E   S   S   I   E   E   C   R   I 1423                                           1470
TTAGACAGTGGGGTGTGAGAGCCTGTTCGCACGACGAAGATGCTGGGGTC
434                                            449
   R   Q   W   G   V   R   A   C   S   H   D   E   D   A   G   V
```

*FIG. 4C*

```
1473                                            1520
ACTTGCACTACATAATGCATCATATTTTCATTCACATTTTTTAAACTGTT
450
T     C    T    T   *

1523                                            1570
ATAAAGTGATTTTTTTCCTTTGCTTCACTAAAATCAGCTTAATTAATATT
1573                                            1620
TAAGAAACTAAGAATTTTATCCACAGAAAAGGAATATTTAAAAATCACTG
1623                                            1670
GATAAACATATAAAATAGCTTCATATTTGCTTCAAATACCAGAACCATTT
1673
CAACTTCTGTAGGTTTTTAAGTGGCTCGTGCCGAATTC
```

*FIG. 4D*

A. DiI-Ac-LDL-UPTAKE    B. IgG-DI IMMUNOBLOT
① DiI-Ac-LDL Alone
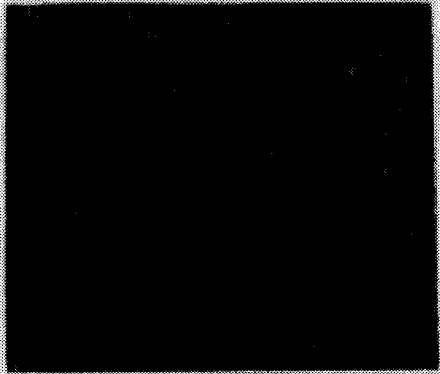
② With Excess Unlabeled Ac-LDL
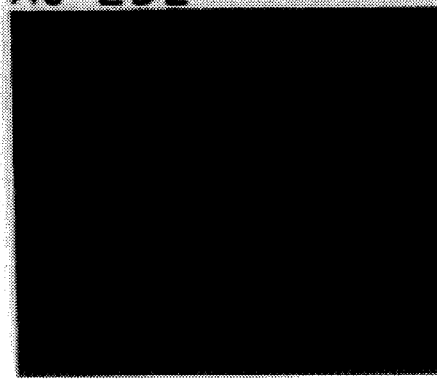
*FIG. 8*

SCAVENGER RECEPTOR PROTEIN AND ANTIBODY THERETO

The U.S. Government has rights in this invention pursuant to NIH Grant No. 5R01HL33516-03.

REFERENCE TO RELATED APPLICATION

This application is a continuation of application Ser. No. 07/997,113, filed Dec. 24, 1992, now abandoned, which is a continuation of application Ser. No. 07/391,486, filed Aug. 9, 1989, now abandoned, which is a continuation-in-part of application Ser. No. 07/272,002, filed Nov. 15, 1988, now abandoned.

BACKGROUND OF THE INVENTION

The technical field of this invention is devices and methods for the diagnosis and treatment of atherosclerosis, and, in particular, devices and methods utilizing receptor proteins associated with atherosclerotic plaques and/or monoclonal antibodies thereto.

Atherosclerosis is a disease which causes the thickening and hardening of the arteries, particularly of the larger arteries. It is characterized by raised fibrous plaques or lesions within the arterial lumen which form as the result of the deposition of plasma cholesterol and low density lipoproteins (LDL).

Key cellular components of the atherosclerotic plaque are foam cells which are derived from phagocytic macrophages of monocytic origin. Macrophages and foam cells have surface receptor proteins which have an affinity for circulating LDL, and which are directly responsible for the receptor-mediated ingestion, or endocytosis, of such material.

These cells also have a receptor-mediated ability to bind and endocytose chemically modified LDL, such as acetylated-LDL (Ac-LDL), acetoacetylated LDL (AcAc-LDL), and oxidized LDL (Ox-LDL), as well as a limited range of other negatively charged macromolecules. This receptor activity has been found to be inducible in monocytes and macrophages under certain conditions, and has been implicated in the formation of foam cells, and hence of atherosclerotic plaques (Goldstein et al. vol. 76, *Proc. Natl. Acad. Sci.* (USA), pp. 333–337 (1980); Brown et al. vol. 52, *Ann. Rev. Biochem.*, pp. 222–226 (1983)).

The injuries or deformities of the arterial lumen caused by the plaque and associated deposits result in occluded blood flow, and ultimately in a number of related conditions if left untreated, such as, angina, cerebral ischemia, renal hypertension, ischemic heart disease, stroke, and diseases of other organs. Coronary atherosclerosis is still the leading cause of death in the United States and in other industrially advanced countries.

Unfortunately, there are no existing diagnostic methods which can reliably detect these diseases. The early stages of atherosclerosis and related vascular diseases often have no clinical manifestations. Because lifestyle changes, drug therapy, and other means exist for delaying or reducing vascular occlusion or the stresses on various body organs which result from atherosclerotic lesions, the early detection of atheromatous plaques would be of considerable value in permitting preventive intervention at a time when it can be most effective.

Arteriography is the conventional approach to diagnosing advanced vascular disease. This procedure involves the imaging of obstructions in the arteries via catheterization and the injection into the bloodstream of radioopaque substances. However, significant morbidity can result from this procedure due to the increased chances of infection, perforation of the artery, arrhythmia, stroke, and infarction. Because of the risks involved, arteriograms typically are reserved for individuals with advanced or acute atherosclerotic disease, ruling out this method for preventative therapy.

A variety of less invasive techniques for the diagnosis of vascular injury and disease have been used. These techniques include plethysmography, thermography, and ultrasonic scanning. (For a review of these procedures, see Lees and Myers, Vol. 27, *Adv. Int. Med.*, pp. 475–509 (1982)). However, none of these imaging techniques have achieved clinical acceptance.

Other non-invasive approaches to the diagnosis of vascular injury include the administration of injectible, detectible agents to the vascular system of a patient which are capable of recognizing, binding to, and/or being internalized by, atherosclerotic lesions. Such procedures include the administration of hematoporphyrin (as described in U.S. Pat. No. 4,577,636, issued to Spears), monoclonal antibodies (EPO 85402359.5 issued to Takano), or magnetic particles capable of being inductively heated (as described in U.S. Pat. No. 4,359,453 issued to Gordon).

Because LDL is known to be deposited in atherosclerotic plaques, methods employing labelled LDL have been utilized to target plaques (see, for example, U.S. Pat. Nos. 4,647,445 and 4,660,563 issued to Lees). A disadvantage to these methods is that several days are typically required to isolate LDL from the patient's blood and to label them. Often, such a delay in diagnosis and subsequent treatment is detrimental for critically ill patients. Furthermore, an additional risk of viral infection can arise if donor blood is employed as an LDL source.

Consequently, there exists a need for better non-invasive techniques and reagents capable of detecting, mapping, and treating early, non-stenosing, non-flow-disturbing atherosclerotic arterial lesions.

Accordingly, it is an object of the present invention to provide methods for the early detection of atherosclerosis and other related vascular diseases. It is also an object of the present invention to identify a component of the arterial plaque which is key in detecting and mapping an abnormal region of the vascular system, or a region predisposed to atherosclerosis. Yet another object of the invention is to provide a detection method which is non-invasive. A further object of the present invention is to provide devices and methods for locating and quantitating the extent of arterial plaque build up. Another object is to provide a method for treating atherosclerosis.

SUMMARY OF THE INVENTION

Receptor proteins, antibodies thereto, and methods and devices utilizing such receptor proteins and antibodies are disclosed herein for the detection and treatment of atherosclerosis. A new receptor protein has been discovered which is capable of binding chemically modified forms of LDL such as acetyl-LDL (Ac-LDL). This receptor protein is found on the surface of macrophages and plaque-forming components. The term "plaque-forming component" is used herein to encompass cells associated with the plaque and/or involved in its genesis such as foam cells, macrophages, and monocytes.

The new receptor protein, referred to hereinafter as the "scavenger receptor protein", or the "receptor protein" has an apparent molecular weight on SDS-polyacrylamide gels of about 220,000 daltons (220 kD), and a binding affinity for Ac-LDL of about 0.5 micrograms per milliliter. It is further characterized as being a trimer of subunits, each of which having an apparent molecular weight on SDS-polyacrylamide gels of about 77 kD, and as including an asparagine (Asn)-linked carbohydrate chain.

In addition, it appears that this novel receptor protein includes not only a region or domain which spans the membrane followed by an alpha-helical triple coiled coil domain, but also an extracellular collagen domain. The term "collagen domain" is used herein to encompass a region of a polypeptide which is substantially analogous to that of collagen or an analog or portion thereof. This collagen domain is found in each of the three subunits.

The present invention includes a substantially pure scavenger receptor protein and an active fragment, analog, and derivative thereof. It also includes DNA sequences including sequences encoding at least a portion of the receptor protein, and active fragments, analogs, derivatives, and subunits thereof.

Further, invention includes a binding reagent with an affinity for the scavenger receptor protein or specific portion thereof. In a preferred embodiment, a monoclonal antibody is disclosed as a binding agent with a specific affinity for the scavenger receptor protein. Such a device could be used to bind various molecules for which the receptor proteins, or fragments or analogs thereof, have affinity.

In one aspect of the invention, a device for assay or purification purposes is disclosed which includes a plurality of scavenger receptor proteins, or fragments or analogs thereof, linked to a support. The invention also includes a device for assay or purification which includes a plurality of binding reagents with an affinity for the scavenger receptor protein, linked to a support.

In other aspects of the invention, methods utilizing the diagnostic properties of the scavenger receptor protein and the binding reagent thereto are also disclosed. For example, a method of detecting an atherosclerotic plaque is described. In this method, the binding reagent is coupled to a labelling means to form a conjugate. The conjugate is then administered to the vascular system of a subject where it is allowed to bind to the scavenger receptor protein associated with a plaque and/or a plaque-forming component. The presence and location of the labelling means in the vascular system of the subject is then determined, as they are indicative of the presence of an atherosclerotic plaque.

The present invention has therapeutic utility as well. For example, one embodiment includes a method of treating atherosclerosis by the selective delivery of a therapeutic agent to a plaque. In this application, a therapeutic agent is coupled to a binding agent having a specific affinity for the scavenger receptor protein, thereby forming a conjugate therapeutic agent. The conjugate is then administered to the vascular system of the subject where it binds to the receptor protein and delivers the therapeutic agent to the plaque or plaque-forming component.

In further aspects of the invention, methods utilizing antagonists of the scavenger receptor protein are disclosed for treatment of vascular disease.

The invention will next be described in connection with certain illustrated embodiments. However, it should be clear that various modifications, additions, and subtractions can be made without departing from the spirit or scope of the invention.

DESCRIPTION OF THE DRAWINGS

The foregoing and other objects of this invention, the various features thereof, as well as the invention itself may be more fully understood from the following description when read together with the accompanying drawings in which:

FIGS. 3A–C are a schematic representation of the nucleic acid sequence and corresponding amino acid sequence of a portion of the protein illustrated in FIG. 2;

FIGS. 4A–D are a schematic representation of a composite nucleic acid sequence and the corresponding amino acid sequence of another overlapping portion of the protein;

FIG. 8 is a photographic representation of (A) a fluorescence photograph demonstrating the ability of macrophages to take up fluorescent labelled acetyl-LDL in the absence (1) or presence (2) of excess unlabelled acetyl-LDL; and (B) the susceptibility of the scavenger receptor protein to trypsin digestion;

DETAILED DESCRIPTION

The scavenger receptor protein is differentially expressed in various tissues. It can be isolated from various organs and, in particular, from mammalian liver and lung specimens by established purification methods. These procedures include, for example, differential centrifugation, detergent extraction of isolated membrane fractions, ion exchange or exclusion chromatography, and gel chromatography.

Alternatively, purification methods employing an antibody which has a specific affinity for the receptor protein may be employed. For example, the receptor protein may be purified by affinity chromatographic methods in which the antibody is bound to an immobilized matrix or support material in a column; the receptor protein may also be immunoprecipitated from a heterogeneous solution using an anti-receptor protein antibody. Using this methodology, the receptor protein may also be isolated from mammalian foam cells and plaque-forming components such as macrophages.

Figure 1:
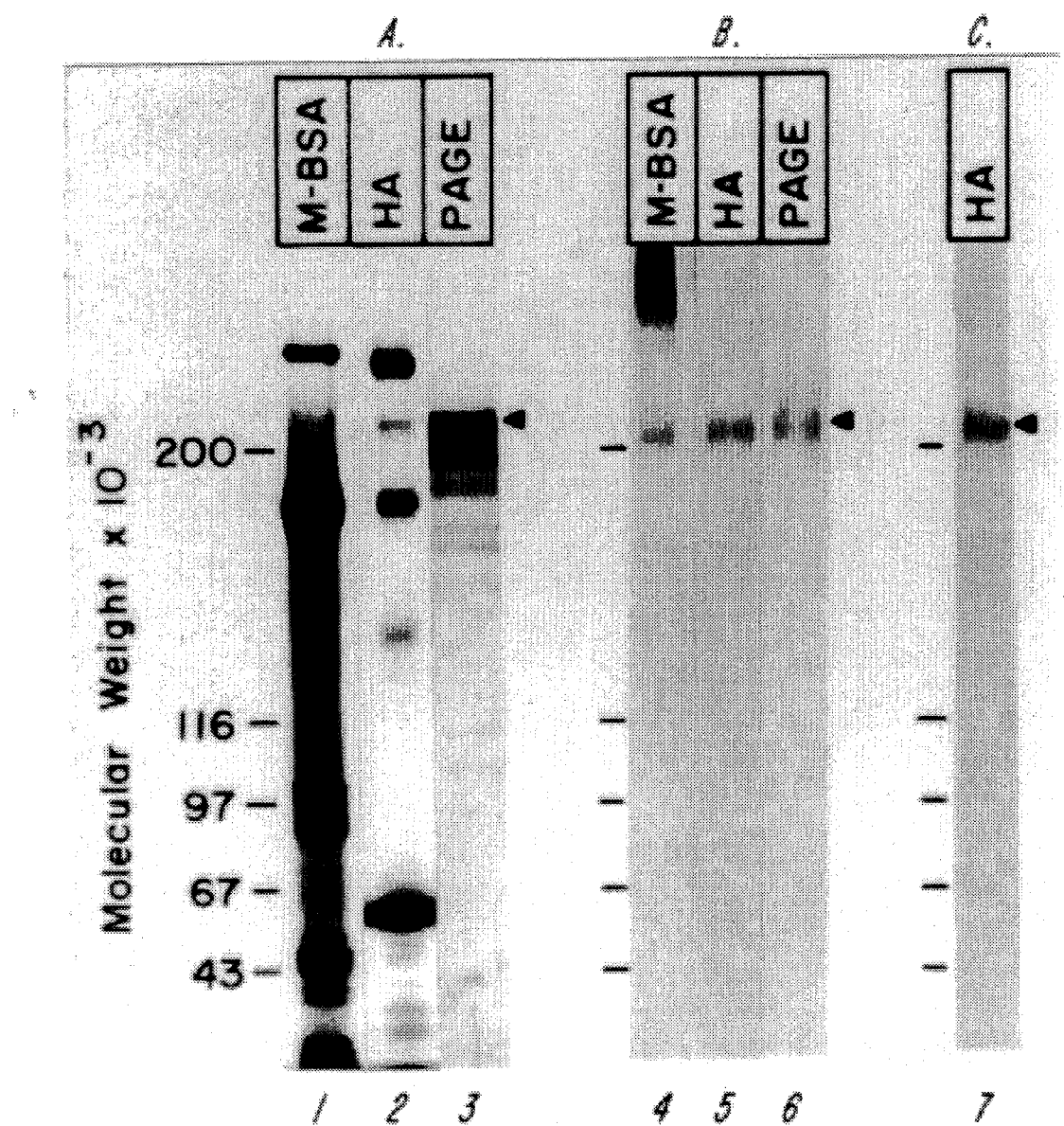
FIG. 1 is a photographic representation of a non-reducing SDS gel of the partially purified scavenger receptor protein which has been silver stained (A); ligand blotted (B); and immunoblotted (C)
Figure 2:
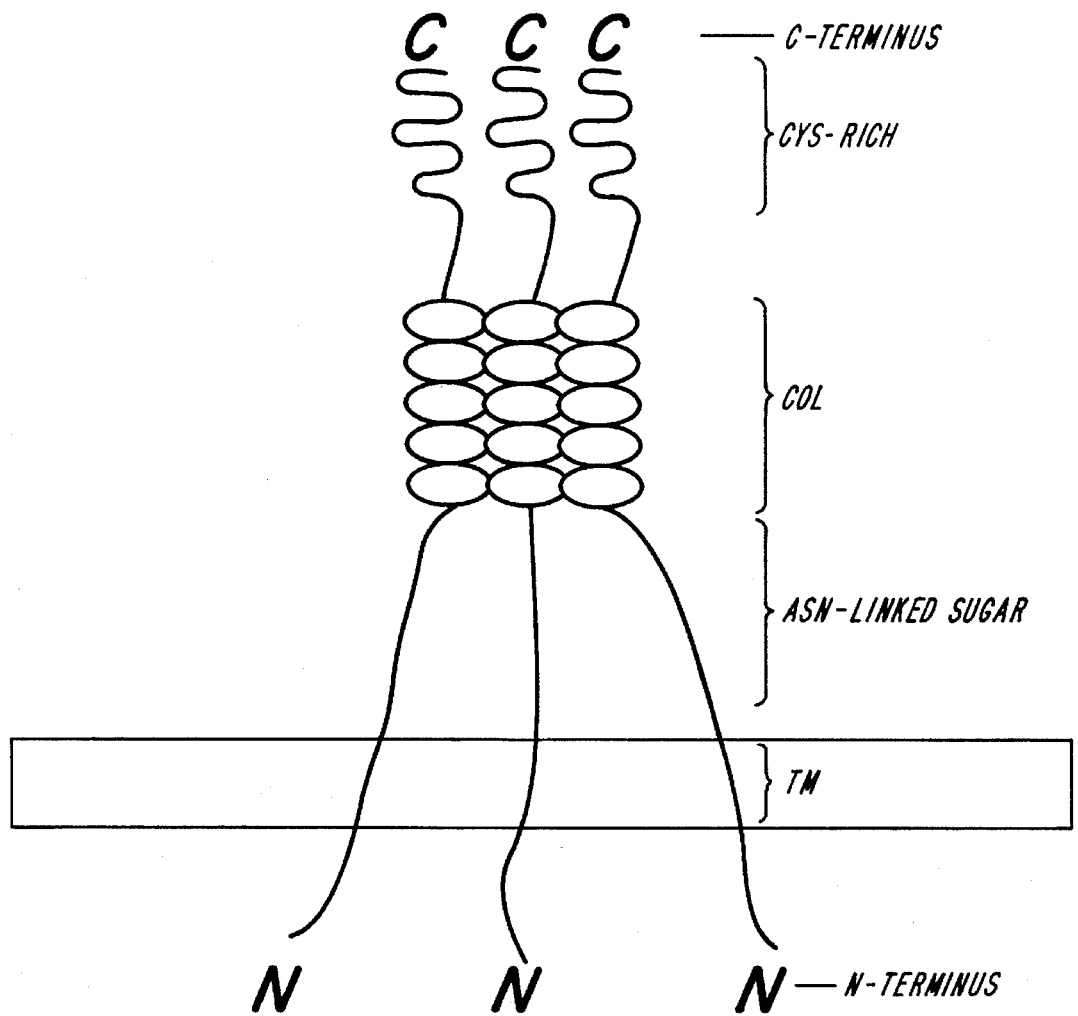
FIG. 2 is a schematic representation of the scavenger receptor protein and its domains.

Using these isolation methods, the scavenger receptor protein has been purified to at least near homogeneity. The protein has an apparent molecular weight on SDS-polyacrylamide gels of about 220 kD (FIG. 1A), and a binding affinity for Ac-LDL. It consists of three seemingly identical subunits, each of which has an apparent molecular weight of about 77 kD (FIGS. 1 and 2), and each apparently having a number of different domains (i.e., Cys-rich domain, collagen domain, asparagine-linked sugar domain, transmembrane domain, and cytoplasmic domain) which are depicted in FIG. 2.

As detailed below, a major portion of the amino acid sequence of the protein has been derived from the nucleic acid sequence of a gene encoding the protein. However, because more than one nucleotide triplet (codon) can encode a single amino acid, a number of different nucleotide sequences can encode a single protein. Hence, the peptide fragment disclosed herein may be encoded by nucleic acid sequences which are functionally equivalent to the one shown above, and which may also be prepared by known synthetic procedures. Accordingly, the invention includes such functionally equivalent nucleotide sequences. In addition, one skilled in the art, knowing the amino acid sequence of the receptor protein, could synthetically or biosynthetically prepare a functionally equivalent analog of the receptor protein of the invention having substantially the same biological activity. In particular, fragments of the protein, especially portions of the extracellular domain, can be obtained for the disclosures herein without undue experimentation.

Thus, the scope of the invention includes the amino acid sequence and corresponding nucleic acid sequence depicted herein, as well as all functionally equivalent amino acid sequences (and corresponding nucleic acid sequences) for molecules with substantially the same scavenger receptor protein biological activities.

Furthermore, those skilled in the art of recombinant DNA technology can use a nucleic acid sequence encoding the receptor protein or a fragment thereof to produce a protein, fragment thereof, or an analog thereof in an appropriate microbial or mammalian host cell. For example, the sequence may be fused into an expression system such as a vector which is suitable for transforming or transfecting a eucaryotic (yeast or mammalian) or prokaryotic (bacterial) host cell. These standard procedures have been followed to produce well-known proteins such as insulin, interferons, human growth hormone, and the like. Similar procedures, or obvious modifications thereof, can also be employed to prepare the scavenger receptor protein, and fragments or analogs thereof proteins in accord with the subject invention.

Using such recombinant DNA methodologies, several clones were prepared which encode at least part of the scavenger receptor protein. Clone 3 encodes at least the membrane spanning (TM) domain and the collagen (Col) domain, as well as an asparagine (Asn)-linked sugar domain (N-linked sugar) including a number of potential sugar linkage sites. The nucleic acid sequences and corresponding amino acid sequence of clone 3 is shown in FIGS. 3A–C wherein the first underlined amino acid sequence is that of the membrane spanning domain, the second underlined sequence is that of the collagen domain, and overlined residues 82–84, 101–103, 142–145, 183–186, 220–222, 248–250, 266–268 are the potential sugar linkage sites within the Asn-linked sugar domain.

Clones 7, 12, and 13 include some or all of these domains as well as at least a portion of a cysteine rich domain. A composite nucleic acid sequence and corresponding amino acid sequence of these clones is shown in FIGS. 4A–D.

TABLE 1 illustrates the location of the various domains within the amino acid sequence of the scavenger receptor protein.

TABLE 1

| amino acid # | Domain | Estimated Mass* |
|---|---|---|
| 1–50 | Cytoplasmic | 5,740 |
| 51–76 | Transmembrane | 2,766 |
| 77–271 | Asn-linked Sugar | 22,480 |
| 272–343 | Collagen | 6,795 |
| 341–453 | Cys-Rich | 12,275 |
| | | 50,056 total |

*based on the molecular weight of the individual amino acids

Figure 6:
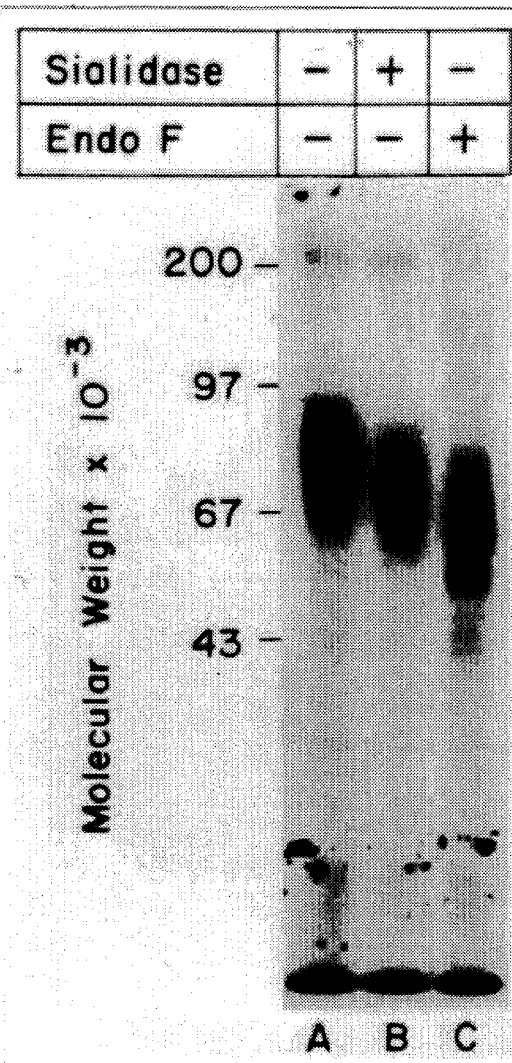
FIG. 6 is a photographic representation of immunoprecipitated 77 kD subunit of the receptor protein which has been digested with sialidase (B) or endoglycosidase F (C) prior to reducing SDS-PAGE.

Each subunit has at least one asparagine (Asn)-linked carbohydrate chain determined by treatment with various deglycosylation enzymes (FIG. 6). The assignment of the Asn-linked sugar domain is based on the presence of potential Asn-linked sugar attachment sites from the cDNA sequence shown in FIGS. 3A–C, and the finding that several of these show no detectable Asn in the protein sequence, suggesting that the Asn groups are indeed glycosylated. By analysis of its amino acid sequence, this domain appears to have an alpha-helical triple coiled coil structure.

The assignment of residues 341–453 as a Cys-rich domain is based on the fact that it contains multiple Cys amino acids. In addition, because this domain is the most distal external domain, and because several other known cell surface receptors have Cys-rich ligand binding domains, this domain may also serve as a ligand binding site. However, since the collagen domain is positively charged and since the ligands are often negatively charged, the collagen domain alternatively or additionally may participate in ligand binding. The same may be true for a portion or all of the alpha helical triple coiled coli in the Asn-linked sugar domain.

The membrane spanning domain of the scavenger receptor protein includes the amino acid sequence:

Thr—Ala—Leu—Ile—Thr—Leu—Thr—Leu—Ile—Val—Phe—
Val—Val—Leu—Val—Pro—Ile—Ile—Gly—Ile—Val—Ala—
Ala—Gln—Leu—Leu.

The collagen domain includes the amino acid sequence:

Gly—Pro—Pro—Gly—Pro—Pro—Gly—Glu—Lys—Gly—Asp—
Arg—Gly—Pro—Pro—Gly—Gln—Asn—Gly—Ile—Pro—Gly—
Phe—Pro—Gly—Leu—Ile—Gly—Thr—Pro—Gly—Leu—Lys—
Gly—Asp—Arg—Gly—Ile—Ser—Gly—Leu—Pro—Gly—Val—
Arg—Gly—Phe—Pro—Gly—Pro—Met—Gly—Lys—Thr—Gly—
Lys—Pro—Gly—Leu—Asn—Gly—Gln—Lys—Gly—Glu—Lys—
Gly—Ser—Gly.

The finding of a collagen-like domain (collagen domain) is consistent with the fact that the scavenger receptor is a trimer. Collagen domains are known to form triple helical trimers in those molecules which have such domains (e.g., collagens, C1q, acetylcholine esterase, serum mannose binding proteins, and lung surfactant protein). This is also true of the alpha helical triple coiled coil in the Asn-linked sugar domain.

The proposed orientation of the receptor shown in FIG. 2 (N-terminus inside, C-terminus outside) is based on the following: 1) there is only one membrane spanning domain; 2) there is no N-terminal signal sequence (presumably, the transmembrane domain is also the signal for membrane insertion); 3) the Asn-linked sugar domain and the collagen domain are expected to be extracellular since the domains have never been found to be cytoplasmic on other proteins); and 4) the charged amino acids surrounding the transmembrane domain have a polarity consistent with the protein being N-terminus in, C-terminus out.

The scavenger receptor protein, having several extracellular domains, allows for the design of reagents which recognize and bind to a particular domain or portion thereof, perhaps thereby modifying the activity of the receptor. Such reagents include, for example, various drugs and binding molecules. Binding proteins which have an affinity for the receptor protein include, for example antibodies, and preferably, monoclonal antibodies. Antisera raised to the purified scavenger receptor protein or a portion thereof, or antibodies purified from the antisera, can be prepared using well known protocols including injection of the purified protein or fragment, or analog thereof, preferably with Freund's adjuvent, into an appropriate mammalian host animal such as a rabbit, goat, or mouse. Preferably, however, monoclonal antibodies are prepared to the scavenger receptor protein, or active fragments of such antibodies, can be generated by applying generally known cell fusion techniques (cf. G. Kohler, C. Milstein, Vol. 6, *Eur. J. Immunol.*, pp. 511–519 (1976); M. Shulman et al., Vol. 276, *Nature*, pp. 269–270 (1978)), herein incorporated by reference) to obtain a hybridoma producing the antibody, by deriving a monoclonal antibody from the hybridoma, and (optionally) by subjecting the monoclonal antibody to proteolysis to obtain an active fragment such as Fab.

For example, monoclonal antibodies can be prepared by obtaining mammalian lymphocytes (preferably mouse spleen cells), committing the lymphocytes to produce antibodies (e.g., by immunizing the mammal with the particular antigen of interest beforehand), fusing the lymphocytes with myeloma (or other immortal) cells to form hybrid cells, and then culturing a selected hybrid cell colony in vivo or in vitro to yield antibodies which are derived from a single clone, and therefore, are identical in structure and specificity.

Alternatively, an antibody molecule of the appropriate specificity, or an active analog or fragments thereof may be produced synthetically in a protein synthesizer, or may be produced by recombinant means in genetically engineered cells.

Serum samples from the immunized animal can be taken and analyzed by an enzyme linked immunoabsorbent assay ("ELISA") or the like for antibody reaction with the immunization agent. Animals that exhibit antibodies titers are sacrificed and their spleens homogenized. Alternatively, the spleen cells can be extracted and the antibody-secreting cells expanded in vitro by culturing with a nutrient medium. The spleen cells are then fused with myeloma (or other immortal) cells. The hybridomas so produced are screened to select a cell line producing antibodies which react with the receptor protein. Large scale antibody production can be obtained from such receptor protein-producing cell lines by various techniques, including the induction of ascites tumors (e.g., after priming with pristane) and the purification of such antibodies from the ascites fluid by Protein A-Sepharose affinity chromatography.

For a further description of general hybridoma production methods, see, e.g., Oi and Herzenberg, "Immunoglobulin-Producing Hybrid Cell Lines" in *Selected Methods in Cellular Immunology* (Mishell and Shiigi, Ed., W. H. Freeman & Co., pp. 351–372 (1980); and Scearce and Eisenbarth, "Production of Monoclonal Antibodies . . . " in Vol. 103, *Methods in Enzymology*, pp. 459–469 (1983), herein incorporated by reference. Human antibodies (i.e., those obtained from human-human or human-animal hybridoma) can be used as well as animal antibodies. For descriptions of human hybridoma production techniques, see, e.g., U.S. Pat. No. 4,451,570 issued to Royston et al; U.S. Pat. No. 4,529,694 issued to Lazarus et al.; and Zurawski et al., "Continuously Proliferating Human Cell Lines Synthesizing Antibody of Predetermining Specificity" in *Monoclonal Antibodies* (Plenum Press, New York (1980)), also incorporated by reference.

Active fragments can be derived from the monoclonal antibodies disclosed herein by a number of techniques. For example, purified monoclonal antibodies can be cleaved with a proteolytic enzyme such as pepsin, and then be subjected to HPLC gel filtration. The appropriate fraction containing the desired fragment such as, for example, an Fab fragment, can then be collected and concentrated by membrane filtration or the like. For further description of general techniques for the isolation of active fragments, see, for example, Khaw et al., Vol. 23, *J. Nucl. Med.*, pp. 1011–1019 (1982), herein incorporated by reference.

The antibodies and fragments used herein can be labelled with radioactive tags such as radioisotopes by a variety of techniques. For example, the biologically active molecules can also be labelled with a radioisotope via conjugation with the cyclic anhydride of diethylenetriamine penta-acetic acid (DTPA) or bromoacetyl aminobenzyl ethylamine diamine tetra-acidic acid (BABE) (Hnatowich et al., Vol. 220, *Science*, pp. 613–615 (1983); and Meares et al., Vol. 142, *Analytical Biochemistry*, pp. 68–78 (1984), incorporated by reference).

The scavenger receptor protein and the binding proteins of the present invention can be used for a variety of diagnostic and therapeutic purposes. In a simple embodiment, soluble receptor proteins are harvested and purified from eucaryotic cells which are preferably mammalian, or from eucaryotic or prokaryotic cells engineered by recombinant means to produce such proteins, and used in both radiolabelled and unlabelled states in competitive binding assays to test for the presence of the receptor. The receptor protein, or fragments or analogs thereof, binding proteins thereto can also be fixed to inert supports for purification and assay purposes. For example, the collagen domain of the receptor protein can be linked to an inert support material for uses in affinity chromatographic methods to isolated lipids and lipid-containing substance such as endotoxin.

Various assay techniques can be practiced employing the reagents disclosed herein, including radioimmunoassays, enzyme immunoassays, heterogeneous and homogeneous assays, enzyme linked immunoabsorbent assays ("ELISA"), and the like.

An exemplary assay for chemically modified LDL or other molecule with an affinity for the receptor protein ("analyte"), can be carried out as follows. The sample (having an unknown concentration of analyte) is first contacted with a known quantity of fixed receptor protein (or analog or a portion of the protein containing the epitope), during which time the analyte in the sample becomes bound to the receptor protein. The fixed support is then treated with a known quantity of radiolabelled analyte which binds to those sites on the fixed support which were unoccupied. Excess label is then washed off, and the quantity of label remaining on the support is inversely proportional to the amount of analyte originally present in the sample.

An alternative assay for analyte can be constructed using the receptor protein fixed to a solid support such as, for example, polystyrene beads or plastic microtiter wells. Samples containing analyte would be incubated with the receptor protein for a time sufficient for binding. The support is then washed to remove any unbound analyte. To detect the bound analyte, a developing reagent consisting of monoclonal or polyclonal antibodies reactive with radiolabelled or enzyme-linked analyte can be used. Alternatively, labelled receptor protein can also be employed. (See, e.g., Roitt, *Essential Immunology*, (Blackwell Press pp. 137–171 (1980), incorporated herein by reference, for further descriptions of immunoassay techniques.

Fixation of receptor protein to solid supports can also be useful as a means for (or additional step in) the purification of crude chemically modified LDL. Similarly, the fixation of monoclonal antibodies specific for the receptor protein can be used in purifying the receptor protein, as well as in recognizing and isolating cells expressing the protein.

The present invention can give rise to a number of therapeutic agents useful in treating various vascular disorders. One class of such compounds includes antagonist compounds or binding reagents which would occupy the affinity sites on the macrophages and monocytes, blocking the binding of chemically modified LDL, and hence, serving as an inhibitor of foam cell development and plaque formation. Useful antagonist compounds include antibodies and preferably, monoclonal antibodies, (or active fragments, analogs, and derivatives thereof) specific for the receptor protein, itself, or portions of the protein (i.e. the extracellular domain) which include the chemically modified LDL binding site. Other useful antagonists include analogs of Ac-LDL or analytes which can bind to the receptor protein without triggering its morphogenesis to foam cells.

The receptor protein, or fragments thereof containing at least an extracellular domain, can also be useful as sequestering agents which would remove chemically modified LDL and other analytes from the blood stream without effecting macrophages, monocytes, or foam cells directly.

The receptor protein can also be useful in designing highly specific drug delivery systems to treat atherosclerosis. The ability of the receptor protein of the foam cell to endocytose various molecules can be exploited to deliver anti-viral agents, metabolites, anti-metabolites, and other therapeutic agents across the cytoplasmic membrane of the foam cell in the plaque. In such instances, the therapeutic agent would be coupled to a macromolecule that is recognized by the receptor protein, enabling the conjugate to become bound to, and ultimately endocytosed, by the foam cell in the plaque. Useful macromolecules for this purpose include Ox-LDL, Ac-LDL, and AcAc-LDL. A synthetic or genetically engineered macromolecule could also be employed.

An antagonist of the receptor protein may be useful in treating vascular disease. For example, a binding molecule such as an antibody, and more preferably, a monoclonal antibody with an affinity for the receptor protein can be administered to the vascular system of a subject. This antagonist will bind to the receptor protein found on plaque forming components such as macrophages, foam cells, and monocytes, thereby preventing or inhibiting such components from contributing to vascular disease such as developing (more) plaque. The antagonist may be any natural, biosynthetic, or synthetic molecule capable of binding and inhibiting the receptor protein.

The invention will next be described in connection with certain illustrated embodiments. However, it should be clear that various modifications, additions and subtractions can be made without departing from the spirit or scope of the invention.

EXAMPLE 1

Scavenger receptor protein was purified from bovine tissue over 2,000-fold by a combination of maleyl-BSA affinity chromatography (M-BSA), hydroxyapatite chromatography (HAP), and preparative $NaDodSO_4$-polyacrylamide gel electrophoresis (SDS-PAGE) (TABLE 2, Method I). This procedure was performed at 4° C. Membrane proteins from 500 g of bovine liver were prepared essentially by the method of Schneider et al. (Vol. 225, *J. Biol. Chem*, pp. 11442–11447 (1980)), herein incorporated as reference. The proteins were resuspended in 500 ml of 10 mM Tris-HCl, pH 8, 1 mM $CaCl_2$, 0.15 M NaCl and 1 mM PMSF (Buffer A). They were sonicated twice, and then dissolved by the addition of 55 ml of 20% Triton X-100 with stirring for 30 min. Insoluble material was removed by centrifugation (33,000 rpm, 1 hr, Beckman Type 35 rotor). The supernatant (500 ml) was applied at 75 ml/hr to an M-BSA-coupled Sepharose 4B column (Pharmacia, 9.8×12 cm, containing about 10 mg of M-BSA/ml of gel) which had been equilibrated with Buffer A containing 1% Triton X-100. The column was washed overnight with the same buffer and then washed with two column volumes of Buffer A containing 40 mM octyglucoside. The receptor protein was eluted with Buffer B (1 M NaCl, 20 mM Tris HCl, pH 8, 1 mM $CaCl_2$, 1 mM PMSF, and 40 mM octyglucoside).

EXAMPLE 2

Filter binding and ligand blotting assays were performed with minor modification, according to the methods of Schneider et al. (ibid.) and Daniel et al. (Vol. 258, *J. Biol. Chem.* pp. 4606–4611 (1983)), respectively, herein incorporated as reference.

Ligand binding specificity was also determined by polynucleic acid affinity chromatography. M-BSA-purified proteins, having 150 ng of Ac-LDL binding activity in 4 ml of Buffer A containing 40 mM octyl glucoside, were applied to polynucleic acid coupled agarose columns (AG-POLY series, prepacked column, Pharmacia). After washing with the same buffer, the bound proteins were eluted with 5 ml of Buffer B.

Cellular scavenger receptor protein activity was assayed essentially as described by Krieger (Vol. 33., *Cell* pp. 413–422 (1983)), herein incorporated as reference, by measuring the degradation of $^{125}$I-Ac-LDL (2 mg Ac-LDL protein/ml) in the presence or absence of inhibitor (M-BSA, 500 mg/ml).

EXAMPLE 3

The fractions obtained as described in EXAMPLE 1 were tested for their ability to bind Ac-LDL as described in EXAMPLE 2; those containing Ac-LDL binding activity (100 ml) were pooled and concentrated (35 ml) using ultrafiltration (Diaflo membrane PM30, Amicon). The sample buffer was changed to 25 mM potassium phosphate, 40 mM octyglucoside, 1 mM PMSF, pH 6.8 using PD10 desalting columns (Pharmacia). The M-BSA affinity purified fraction (50 ml) was then applied to an Ultrogel-Ha (LKB) column (2.5×13 cm) at a flow rate of 75 ml/hr. The proteins were eluted with a gradient of phosphate buffer (25 mM to 350 mM) containing 40 mM octyglucoside.

The 220 kD protein was recovered at phosphate concentrations between 100 and 200 mM and was further purified by non-reducing SDS-PAGE on a 3–10% acrylamide gradient gel as described by Laemmli (Vol. 227, *Nature* pp. 680–685 (1970)), herein incorporated as reference). FIG. 1 shows the silver staining (A, lanes 1, 2, 3) and Ac-LDL ligand blotting (B, lanes 4, 5, 6) of the purified fractions on non-reducing gels. A 220 kD protein with Ac-LDL binding activity was purified. The protein was electroeluted from the gel in 0.1% SDS, 10 mM Tris-HCl, pH 8 using an ISCO 1750 electrophoretic concentrator. TABLE 2 summarizes these results under Method I.

TABLE 2

| Fraction | Protein | | | |
| --- | --- | --- | --- | --- |
|  | (mg/frac.) | total binding (mg) | Spec. Act. (Ac-LDL/ mg) | Pur. Fac. (X) |
| Method I |  |  |  |  |
| Liver mem. | 21,580 | 107.9 | 0.005 | 1 |
| Maleyl-BSA | 72 | 154.8 | 2.15 | 430 |
| HAP Chrom. | 6 | 62.8 | 10.47 | 2094 |
| Prep. PAGE | 0.025* | ** | ** | ** |
| Method II |  |  |  |  |
| Lung mem. | 22,800 | 136.8 | 0.006 | 1 |
| M-BSA Chrom. | 45 | 121.0 | 2.684 | 427 |
| Immunoaff. | 0.03° | 42.0 | 14030 | 238,000 |

*Estimated from chromogeneity on silver staining of PAGE gels.
**Due to the presence of SDS, the activity could not be determined.
°Estimated from amino acid composition analysis.

Partial purification of the 220 kD protein from other bovine organs or from cells followed essentially the same procedure as for bovine liver, except that all steps were performed on a smaller scale.

The distribution of the 220 kD protein and Ac-LDL binding activity in various bovine organs was examined using immuno- and ligand blotting. There was close correlation of the intensities of staining and of the electrophoretic mobilities (220 kD) of the antibody binding and ligand binding proteins. Ligand binding activities and the amounts of 220 kD protein were high in the liver, lung, spleen and adrenal gland, which are organs known to take up Ac-LDL efficiently in vivo. The intestine, which takes up little Ac-LDL, contained very little 220 kD protein and little binding activity.

EXAMPLE 4

The scavenger receptor protein was purified 238,000-fold by a combination of M-BSA affinity chromatography, and IgG-D1 immunoaffinity chromatography (TABLE 2, Method II). All procedures were performed at 4° C. 100 ml of Buffer C (0.1% SDS, 0.1% sodium deoxycholate, 1% Nonidet P40, 50 mM Tris-HCl, pH 8, 150 mM NaCl, and 1 mM PMSF) were added to M-BSA affinity purified proteins from 500 g of bovine liver or lung in 100 ml Buffer B. The sample was applied to Sepharose 4B (Pharmacia) coupled with IgG-D1 prepared as described below. (4 mg antibody/ ml gel, 1×2 cm) at a flow rate of 50 ml/hr, and recycled overnight. The column was washed consecutively with 50 ml of Buffer C, 50 ml of Buffer D (0.2% Triton X-100, 10 mM Tris-HCl, pH 8), 50 ml of Buffer D containing 2 M NaCl, and 20 ml of Buffer E (40 mM octylglucoside containing 10 mM Tris-HCl, pH 8). The bound proteins were then eluted with 20 ml of Buffer E containing 2 M guanidine thiocyanate. After elution, the buffer was changed to Buffer A containing 40 mM octylglucoside using PD10 columns (Pharmacia). Proteins were stored at −70° C. TABLE 2 summarizes the results under Method II.

EXAMPLE 5

A hybridoma was made by the fusion of mouse myeloma cells (P3X63-Ag8.653) and spleen cells of a mouse which had been immunized with receptor protein protein purified by preparative SDS-PAGE, essentially as described by Oi et al. (ibid.), herein incorporated as reference. 15 mg of receptor protein was used for the initial injection, and 10 mg was used for the booster. Hybridomas secreting antibody were identified by an enzyme immunoassay using 96-well plates coated with hydroxyapatite (HAP)-purified proteins as described by Beisiegel et al. (Vol. 256, *J. Biol, Chem*, pp. 11923–11931 (1981)), incorporated herein as reference, and then by immunoblotting as described by Tsang et al. (Vol. 92, *Methods in Enzymology* pp. 377–390 (1983)), incorporated herein as reference. The hybridomas were subjected to limiting dilution twice and were cultivated in RPMI 1640 medium containing 0.1% fetal calf serum and 1% Nutridoma-NS. The monoclonal antibody IgG-D1, and the control antibody which recognizes a distinct and apparently unrelated 287 kD protein, were isolated from the culture media by Affigel protein A chromatography using a MAPS II buffer kit (Bio Rad).

EXAMPLE 6

Partially purified receptor protein isolated as described in EXAMPLE 1 was subjected to SDS-PAGE and immunoblotting procedures as described by Tsang et al., (ibid.). The immunoblot shown in FIG. 1(C), (lane 7) demonstrates that IgG-D1, raised against the unreduced, gel-purified 220 kD bovine protein, recognizes the bovine 220 kD protein. Reduction abolishes the binding of IgG-D1 and Ac-LDL ligand blotting activity.

EXAMPLE 7

Figure 5:
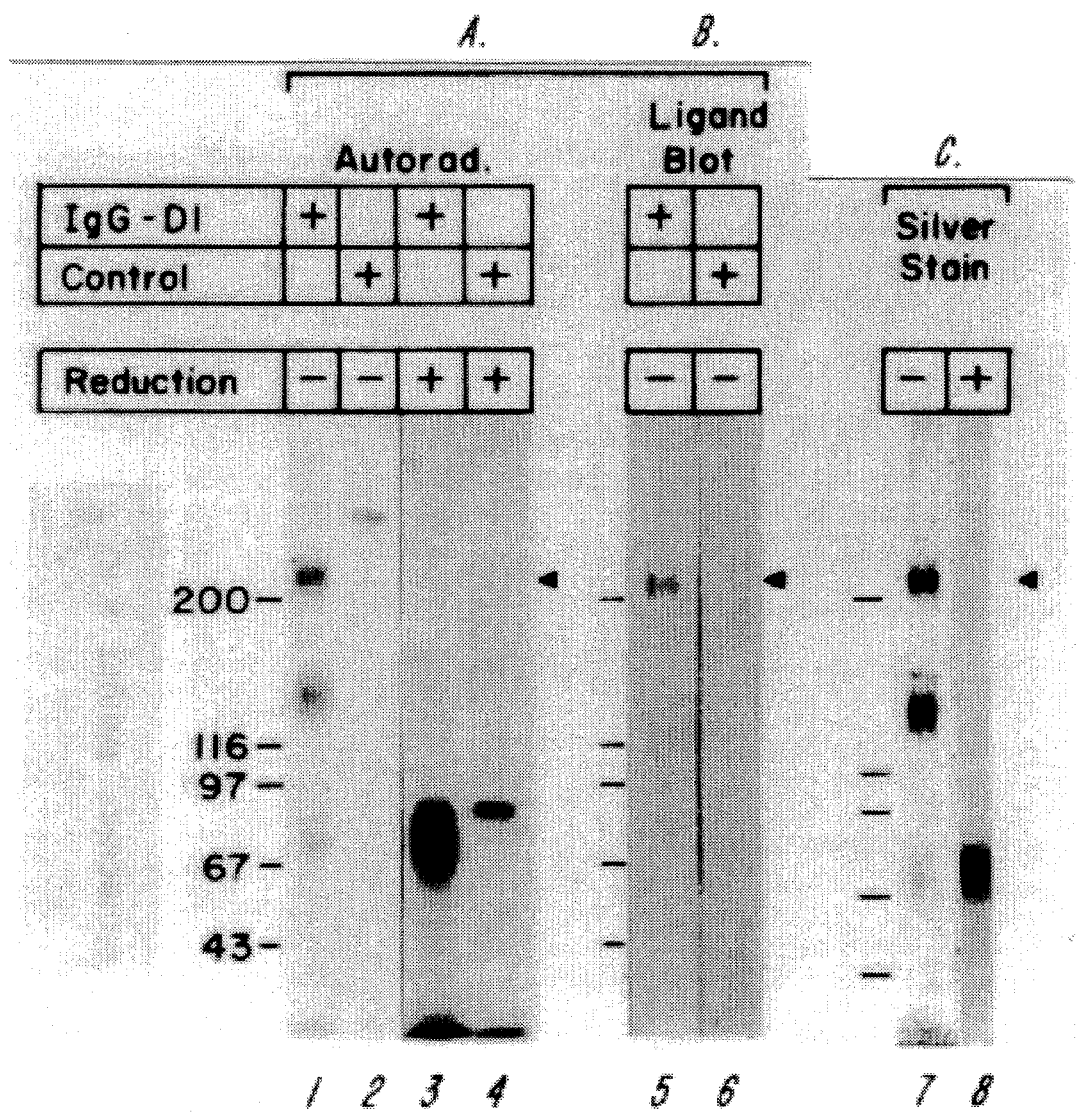
FIG. 5 is a photographic representation of the scavenger receptor protein which has been subjected to immunoprecipitation, non-reducing SDS-PAGE and then to autoradiography (A) or ligand blotting (B), or to immunoaffinity purification followed by non-reducing SDS-PAGE and silver staining (C)

The cell type specificity and tissue distribution of the 220 kD protein and its relation to the Ac-LDL receptor were also studied using immunochemical techniques. Immunoprecipitation was performed essentially as described by Kozarsky et al. (Vol. 102, *J. Cell Biol.*, pp. 1567–1575 (1986)), herein incorporated as references using the monoclonal antibodies obtained as described in EXAMPLE 3, and using the HAP-purified binding protein from bovine liver or lung (2–10 mg Ac-LDL binding activity/mg protein) which had been radioiodinated using Iodobeads (Pearce). The results of immunoprecipitation of $^{125}$I-labelled specimens with IgG-D1 or with control antibody T2D2 are shown in FIG. 5. IgG-D1 specifically precipitated three $^{125}$I-labelled bovine species with apparent molecular weights of 220 kD, 150 kD, and 77 kD (A, lane 1). The immunoprecipitated 220 kD protein was recovered and shown to retain Ac-LDL binding activity by ligand blotting (B, lane 5).

EXAMPLE 8

The scavenger receptor proteins precipitated by IgG-D1 and purified by immunoaffinity chromatography exhibited apparent molecular weights of 220 kD, 150 kD, and 77 kD by non-reducing SDS-PAGE. After reduction they collapsed into 77 kD bands (FIG. 5A, lanes 3 and 4). When the 220 kD and 150 kD proteins, obtained by immunoprecipitation or immunoaffinity chromatography, were individually recovered from preparative gels and then reduced, the apparent mass of each was also converted to 77 kD, indicating that the 220 kD and 150 kD proteins were trimers and dimers of 77 kD subunits.

The carbohydrate characteristics of the receptor protein were determined by subjecting the 77,000 dalton subunit to immunoprecipitation (as described in EXAMPLE 7) followed by digestion with sialidase (Boehringer Mannheim, Indianapolis, Ind.) or endoglycosidase F (GENZYME, Boston, Mass.) as described by Elder et al. (Vol. 79, *Proc. Natl. Acad. Sci. (USA)*, pp. 4540–4544 (1982)) herein incorporated as reference. The resulting protein was then subjected to SDS-PAGE under reducing conditions (FIG. 6). After treatment, its apparent molecular weight was reduced by approximately 5 kD after sialidase treatment, or 13 kD after endoglycosidase treatment, demonstrating the presence of asparagine-linked carbohydrate chains and sialic acids.

The immunoaffinity-purified activity also exhibited apparent molecular weights of 220 kD, 150 kD, and 77 kD by non-reducing SDS-PAGE (FIG. 5C, lane 7).

EXAMPLE 9

Immunohistochemistry was performed on bovine liver samples as follows. Tissue sections (6 mm) were cut on a cryostat at −20° C., placed on glass slides, air dried for 1 hour, and fixed in cold 95% methanol. The sections were incubated with monoclonal antibody IgG-D1 (6 mg/ml) or control mouse IgG. The binding of IgG was visualized using peroxidase-conjugated sheep anti-mouse IgG Fab by 3,3'-diaminobenzidine tetrahydrochloride staining as described by Adamson et al., (Vol. 130, *J. Immunol.* pp. 203–207 (1983)), herein incorporated as reference. Sections were counterstained with methyl green (Sigma).

Figure 7:
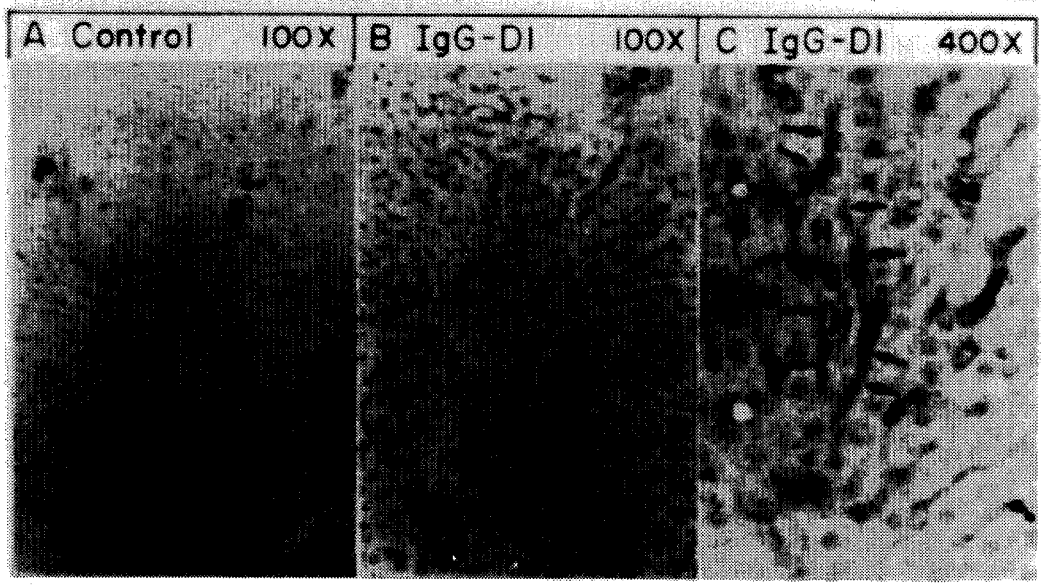
FIG. 7 is a photographic representation of the immunohistochemical localization of the scavenger receptor protein in bovine liver incubated with (A) control antibody, or (B, C) IgG-D1.

FIG. 7 shows the immunohistochemical analysis of frozen liver sections using the anti-bovine 220 kD protein monoclonal antibody IgG-D1. The distribution of the 220 kD binding protein matches that previously described for scavenger receptor protein activity: specific sinusoidal (arrows), but not hepatocyte (H), immunostaining (panels B and C); and very little staining in the area immediately surrounding the central vein (CV). P indicates portal area.

EXAMPLE 10

Cell cultures of macrophages were prepared to test their ability to take up acetyl-LDL. Bovine alveolar macrophages were collected from fresh lung by bronchial lavage with phosphate buffered saline (PBS, 1 liter/lung). They were cultivated with RPMI 1640 medium containing 10% fetal calf serum for 6 hrs at 37° C. in a $CO_2$ incubator, and washed with PBS 6 times to remove non-adherent cells. The uptake of fluorescent Ac-LDL labelled with 1,1'-dioctadecyl-3,3, 3'3'-tetramethyl-indocarbocyanine (DiI) was performed as described by Kingsley et al. (Vol. 81, *Proc. Natl. Acad. Sci. (USA)* pp. 5454–5458 (1984)), herein incorporated as reference.

For immunoblotting, cells from two 150 mm dishes were incubated with trypsin (0.05%) or PBS for 5 min at 37° C., and harvested by scraping. Floating cells were recovered by centrifugation and were mixed with the scraped cells. The cells were then resuspended in 10 ml of ice cold Buffer A. The 220 kD protein, partially purified from the membrane using M-BSA affinity chromatography, was subjected to immunoblotting as described in EXAMPLE 6. The viability of cells, determined by either trypan blue staining (floating cells) or restoration of DiI-Ac-LDL uptake after overnight cultivation (adherent cells), was not significantly affected by the mild trypsin digestion.

Coincident expression of Ac-LDL receptor activity (fluorescent DiI-Ac-LDL accumulation, FIG. 8 panel A) and the 220 kD protein (immunoblotting with IgG-D1, FIG. 8, panel B, lane A) was also detected in cultured bovine aveolar macrophages. Fluorescently labelled Ac-LDL uptake was blocked by the presence of excess unlabelled Ac-LDL (panel A). Immunodetection of the 220 kD protein was prevented by pretreating the macrophages with low, sublethal levels of trypsin (0.05%) for 5 min. at 37° C. (FIG. 8, panel B, lane B). The trypsin sensitivity of this protein in intact cells suggests that some of the 220 kD protein is at least partially exposed at the cell surface.

EXAMPLE 11

The human monocytic leukemia cell line THP-1 was cultivated in RPMI 1640 medium containing 10% fetal calf serum. THP-1 cells were induced to differentiate into macrophage-like cells by cultivation for 3 days in the presence of 200 nM phorbol 12-myristate 13-acetate (PMA). The maleyl-BSA affinity purified membrane proteins from $10^8$ cells treated with or without PMA were subjected to Ac-LDL ligand blotting and filter binding assays as described in EXAMPLE 1.

Figure 9:
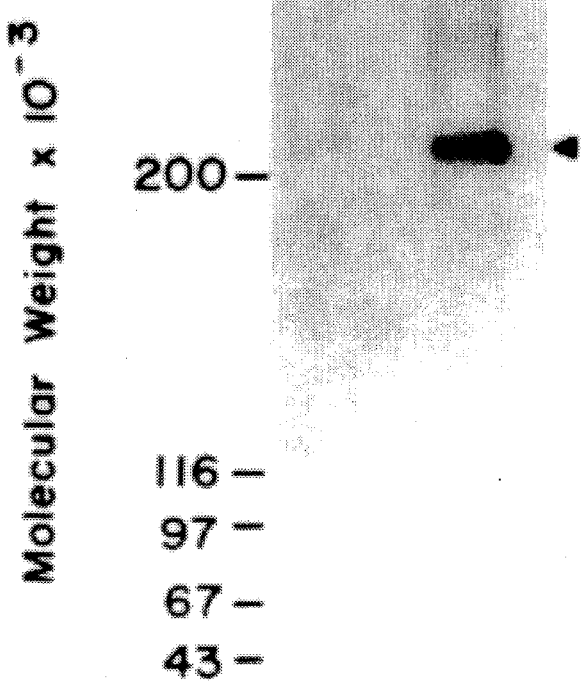
FIG. 9 is a photographic representation of a ligand blot demonstrating the coinduction of the scavenger receptor protein and cellular scavenger receptor-mediated endocytosis in human monocyte (PMA–)/macrophage (PMA+) cell lines.
Figure 10:
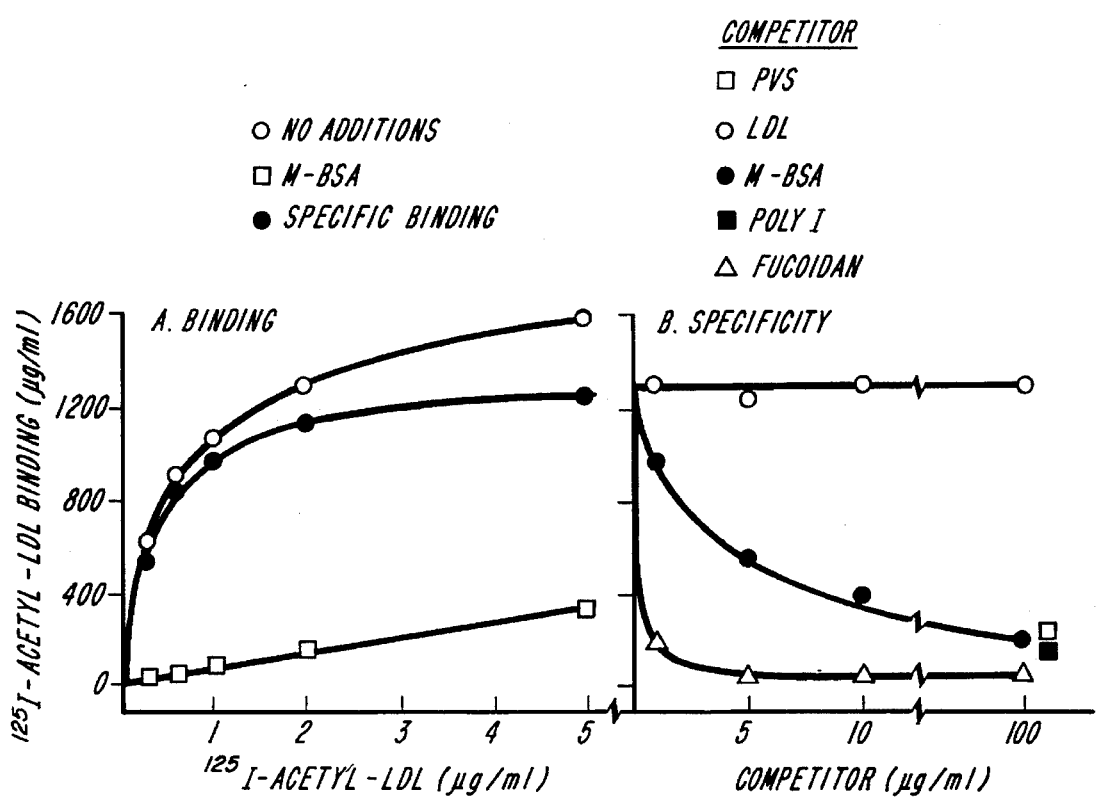
FIG. 10 is a graphic representation of the binding affinity (A) and specificity (B) of acetyl-LDL binding to the affinity purified receptor protein.

Coincident and coordinately regulated expression of acetyl-LDL receptor activity and a 220 kD binding protein were observed in this human cell line. FIG. 9 shows that the phorbol ester induction of receptor activity ($^{125}$I-Ac-LDL degradation assay) is accompanied by a substantial increase in the $^{125}$I-Ac-LDL binding activity of cell membrane proteins (filter binding assay), and by a dramatic increase in the amount of activity of a 220 kD scavenger receptor protein (ligand blot assay). The immunoaffinity-purified receptor protein bound $^{125}$I-Ac-LDL with an apparent dissociation constant of 0.5 mg/ml (0.8 nM) (FIG. 10A). The maximum binding of $^{125}$I-Ac-LDL was about 1.4 mg/mg.

Competition of Ac-LDL binding was measured by preincubating immunoaffinity purified receptor protein/phospholipid complexes in the various concentrations of analyte competitors for 30 min. prior to the addition of $^{125}$I-Ac-LDL (2 mg protein/ml) for 1 hour at 4° C. (Relatively successful analyte competitors were LDL, maleyl-BSA, fucoidan, polyvinylsulfate, and the purine polynucleotides poly[I], poly[I-C], and poly[G] (FIG. 10B).

The purified receptor can also bind Ox-LDL. TABLE 3 demonstrates this activity. The OX-LDL was prepared using the method of Steinbrecher et al. (Vol. 81, *Proc. Natl. Acad. Sci (USA)* pp. 3883–3887 (1984)), herein incorporated as reference. The specific activity was determined by subtracting the binding activity in the presence of competitor (200 ug/ml Ac-LDL) from the activity in the absence of competitor by the liposome reconstitution assay using $^{125}$I-Ox-LDL. These result indicates that the scavenger receptor protein may also play an important role in the metabolism of Ox-LDL.

TABLE 3

| Oxidized-LDL (mg/ml) | Specific Binding of $^{125}$I-Ox-LDL (μg Ox-LDL/mg scavenger receptor) |
|---|---|
| 0.5 | 59 |
| 1.0 | 89 |
| 2.0 | 135 |
| 5.0 | 302 |
| 10.0 | 417 |

EXAMPLE 12

The scavenger receptor protein was further purified using RP-300 (Brownlee Laboratory, Emeryville, Calif.) reverse phase HPLC. The receptor was solubilized in 70% formic acid. It was then cleaved by cyanogen bromide (CNBr) (25 mg/100 ml solution) at room temperature, overnight, resulting in the formation of a number of cleavage fragments. The fragments were chromotographically separated on the RP-300 column.

One of the fragments was isolated and subjected to automated amino acid analysis using an Applied Biosystems amino acid sequencer (Foster City, Calif.). The following amino acid sequence was thereby obtained:

Arg—Ile—Gln—Tyr—Leu—Ser—Asp—Asn—Glu—Ala—
Asn—Leu—Leu—Asp—Ala—Lys—Asn—Phe—Gln.

A second sequence (below) was obtained from a similar CNBr digestion using the gel elctrophoresis/immunoblotting method of Matsudaira (J. Biol. Chem. (1987) 262:10035–10038):

Lys—Leu—Leu—Asn—X—Ile—X—Asn—
Asp—Leu—Arg—Leu—X—Asp—Trp where "X" indicates that the amino acid residue at that position is uncertain. (See FIGS. 3A–C for the relative location of these residues (underscored dots) in the amino acid sequence of clone 3.)

EXAMPLE 13

Methodology for the development and identification of the clones, unless otherwise noted, were standard procedures such as those described in Maniatis et al. (*Molecular Cloning, A Laboratory Model* (1982) Cold Spring Harbor Laboratory) and Davis et al. (*Basic Methods In Molecular Biology* (1988) Elsevier Scientific Publishing Co., Inc., NY).

A. Preparation of cDNA Library

Poly(A)$^+$ mRNA was isolated by acid guanidium thiocyanate/phenol/chloroform extraction as described by Chomczynski (*Anal. Biochem.* (1987) 162:156) from bovine lung, and was used to construct a random primed cDNA library. 6 μg of bovine lung macrophage mRNA and 5 μg of random hexanucleotides were used to synthesize double-stranded cDNA following the general procedure of Gubler and Hoffman (Gene (1983) 25;263). The cDNA so synthesized was ligated to Eco R1 adaptors (Pharmacia), and was then size-fractionated on a 5–20% potassium acetate gradient by centrifugation for 3 hr in an SW60 rotor (Beckman Instruments) at 50,000 rpm. The cDNA fractionating at molecular masses of approximately greater than or equal to 800 base pairs (by agarose electrophoresis) was then ligated into Eco R1 digested λzap (Stratagene), packaged, and subsequently used to infect XL-1 Blue cells (Stratagene). 1.5×10$^6$ primary clones were obtained and amplified.

B. Library Screening and Isolation of cDNA Clones

The library was screened with two pools of 41 mer oligonucleotide probes that included 5-fluorodeoxyuridine (F) (Habener et al. (1988) *Proc. Natl. Acad. Sci.* (USA) 85:1735–1739) according to the amino-acid sequence:

RIQULNSDNEANLLDA.

These pools were divided according to the codon usage at serine. Pool I contained:

5'-ATFCAGTAFFT(F/G)<u>TC(F/G)</u>GAFAAFGA
GGCF/G)AAFFT(F/G)FT(F/G)GAGAFGC-3'.

Pool II contained AGF at the underlined (TC(F/G)) nucleotides shown above for pool I. For each pool, 5×10$^5$ plaques were screened using $^{32}$P end-labelled probes by hybridization at 37° C. and washing at 50° C. in 6×SSC (Maniatis et al. ibid. pp. 447) with 0.1% SDS. Putative positive clones were purified and in vivo excised into picoblue (pBluscript)-derived plasmids (Short, ibid.). The inserts were screened by Southern blot hybridization (Southern (1975) J. Mol. Biol. 98:503) using 4 pools of the 17 mer oligonucleotide:

A(A/G)(A/G)TTNGC(C/T)TC(A/G)TT(A/G)TC, each containing a different nucleotide at the underlined (N) position. Pool III contained:

AT(F/A)CA(G/A)TAFFTTTCTGAFAAFGA(G/A)GC and pool IV contained AGF at the underlined (TC) position of pool III.

Five positive clones were selected and sequenced according to the Sanger method (Sanger et al. (1977) Proc. Natl. Acad. Sci. (USA) 74:5463). These clones have a nucleotide sequence corresponding to the peptide sequence. FIGS. 3A–C show the nucleic acid sequence and corresponding deduced amino acid sequence of clone 3, while FIGS. 4A–D show a composite nucleic acid sequence and corresponding deduced DNA sequence of clones 7, 12, and 13.

C. Sequence Analysis

The sequencing of the cDNA clones indicates that the cDNAs isolated are derived from two different mRNAs. Both of these mRNAs encode identical 347 amino acid N-terminal domains [Met$^1$→ARG$^{347}$]. They differ in this region by one nucleic acid which does not result in an amino acid change. The two mRNAs begin to differ at amino acid position 348. The sequence of clone 3 (FIGS. 3A–C) continues for only 2 additional amino acids before a stop codon is seen. (Arg-Pro-Gly STOP). In contrast, the sequence of clone 7 (FIGS. 4A–D) continues for an additional 106 amino acids.

Clone 3 contains 35 noncoding bases at its 5'end, 1047 bases of coding region, and 965 noncoding bases at its at the 3'end (FIGS. 3A–C). In coding region (* denotes the start of the coding region), amino acid residues 1–50 represent the cytoplasmic domain (Cy), residues 51–76 represent the proposed transmembrane domain (TM), residues 77–271 represent the proposed Asn-linked sugar domain, residues 272–343 represent the proposed collagen domain (Col), and residues 344–349 represent the proposed C-terminal domain (C-term). In FIGS. 3A–C, the residues of the TM domain are underscored (first underscored region); the Asn-linked sugar sites are overscored; the Col domain is underscored (second underscored region); M* is the initiator Met; and the first 19 amino acids making up the peptide used to generate the anti-peptide antibody are underscored with dots (with the exception of Ser$^{138}$, which was later determined to be Lys).

Clone 7 (FIGS. 4A–D) has no 5' noncoding bases, 1359 bases of coding region, and 211 noncoding bases at its 3'end.

D. Expression of cDNA Clones

A clone 3 expression vector pXAcLDLR3 was prepared by excising the clone 3 sequence from the pBluescript product (i.e., the in vivo excision product of the λzap vector) using BAM Hl and Xhol. The resulting DNA fragment was then ligated into the pcDNA1 plasmid (Invitrogen) which had been previously cut with the same restriction enzymes.

On day 0, monkey COS M6 cells (derived from COS 7 cells available from the American Type Culture Collection, Rockville, Md., and a gift from D. Hausman, Dept. of Biology, MIT) were set at $1.5 \times 10^6$ cells/100 mm dish in the standard cell culture medium DMEM (Gibco) containing 10% fetal bovine serum, penicillin, and streptomycin. On day 1, the cells were tranfected following standard procedures (Seed et al. (1987) Proc. Natl. Acad. Sci. (USA) 84:3365–3369). In brief, a transfection cocktail was added to each dish already containing 4 ml DMEM containing 10% Nuserum (Collaborative Research). The cocktail consisted of 10 μl (40 mg/ml) DEAE Dextran solution, (Pharmacia), 40 μl of 10 mM chloroquine (Sigma), and 4 μg clone 3 expression vector XAcLDLR3. The final concentrations in the transfection medium were 10% NuSerum, 100 μg/ml DEAE Dextran, 100 μM chloroquine, and 4 μg/ml vector DNA. After incubation for 4 hr at 37° C., the tranfection medium was removed and the cells treated for 2 min with Hepes buffered saline (HBS: 137 mM NaCl, 5 mM KCl, 0.7 mM $Na_2HPO_4$, 6 mM dextrose, 21 mM Hepes, pH 7.1) containing 10% dimethylsulfoxide (DMSO). The HBS-DMSO solution was removed and the cells refed with standard culture medium (DMEM containing 10% fetal bovine serum and the antibiotics). On day 2, the transfected cells were harvested by trypsin treatment. They were reset into 6-well dishes at a concentration of $1 \times 10^6$ per well for assays performed on day 4, or at a concentration of $0.8 \times 10^6$ per well for assays performed on day 5.

E. Receptor Activity Assay

The ability of the transfected monolayers to degrade 5 μg protein/ml of $^{125}$I-Ac-LDL in the absence (triplicate determinations) or presence (single determinations) of different concentrations of various unlabeled competetitors was measured using the standard assay procedures of Krieger (ibid.).

Figure 11:
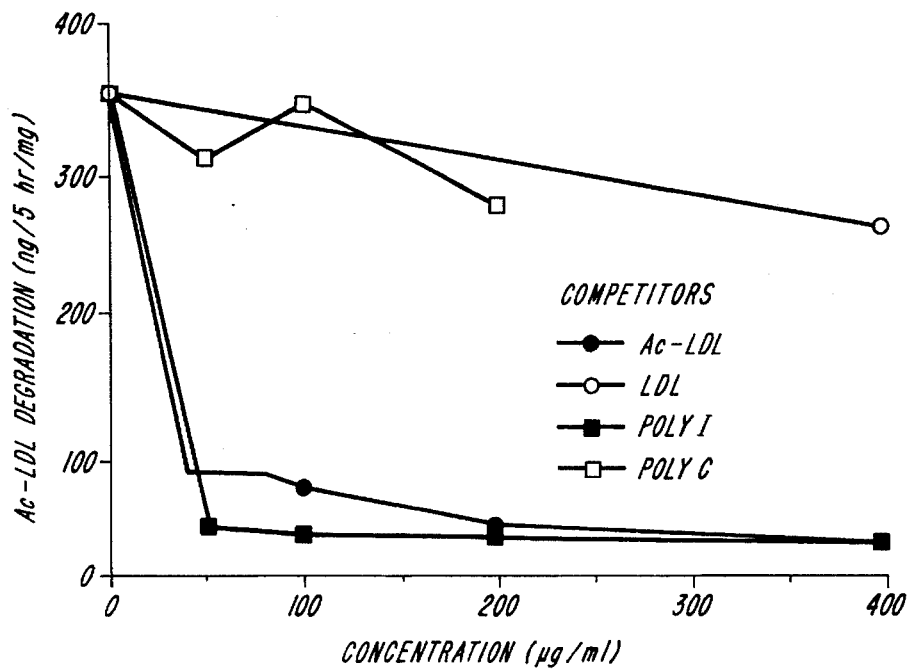
FIG. 11 is a graphic representation of the ability of different concentrations of a number of competitors to inhibit Ac-LDL receptor activity.

The results are shown in FIG. 11. In control cells tranfected with pcDNA which did not contain clone 3, the amount of Ac-LDL degraded was only 5% of that degraded by the pAcLDL3-transfected cells. This experiment demonstrates that high affinity Ac-LDL receptor activity is expressed in cells transfected with an expression vector including clone 3 (pXAcLDLR3).

Figure 12:
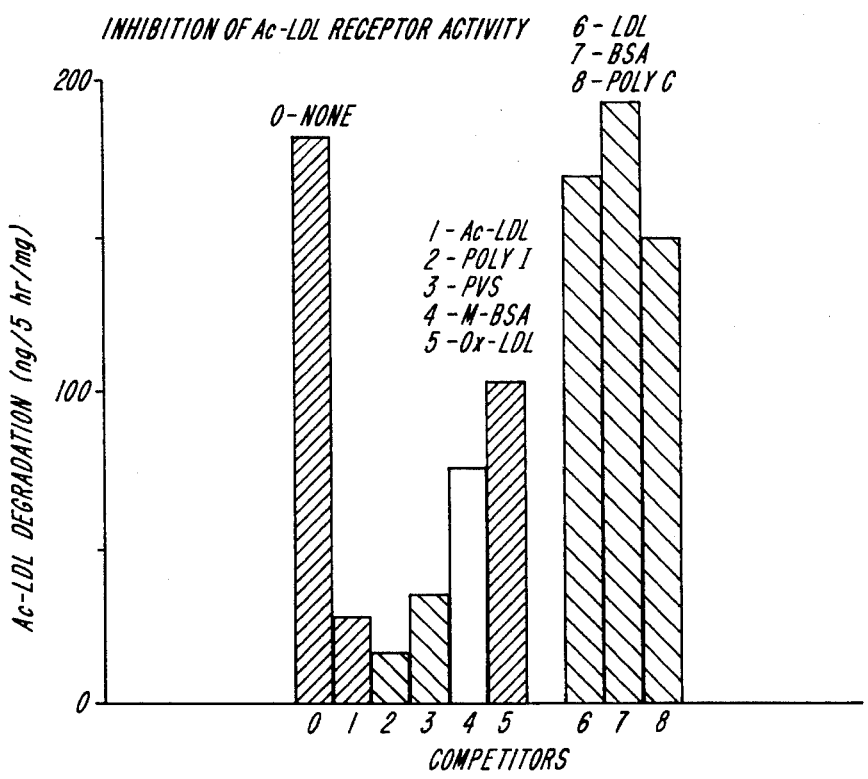
FIG. 12 is a graphic representation of the ability of one concentration of different competitors to inhibit Ac-LDL receptor activity.

In another experiment, cells were prepared and assays were performed as described above except that 400 μg/ml competitor was used. The inhibitors included poly [I], poly [C], LDL, Ac-LDL, maleylated bovine serum albumin (M-BSA), Ox-LDL, BSA, and polyvinyl sulfate (PVS). The results are also shown in FIG. 12. This experiment also indicates that clone 3 can express high affinity Acetyl-LDL receptor activity in cells transfected with the clone 3-containing vector pXAcLDLR3.

F. Tissue and Cell Type-Specific Expression of Ac-LDL Receptor mRNA

The ability of Ac-LDL encoding-clones to be expressed in different cell and tissue types was investigated to determine if the pattern of their expression mirrored that of the expression of the native receptor. Standard Northern (RNA) blot hybridization methods were followed using the collagen domain-encoding fragment of clone 3 as a probe. THP-1 cells were cultivated with or without 200 nM phorbol 12-myristate 13-acetate (PMA) for 3 days to induce them to differentiate into macrophage-like cells (Kodama et al. (1988) Proc. Natl. Acad. Sci. (USA) 85:9238 (Dec.)). Bovine alveolar macrophages were prepared as previously described (Kodama, ibid.). Poly(A)$^+$ RNA (3 μg) from these cells and from various bovine organs was isolated and blotted on a cellulose nitrate membrane. The Xba 1/Sph 1 fragment of a subclone pJAL 5, which includes the sequence encoding the collagen-like domain of clone 3, was $^{32}$P radiolabelled, hybridized at 42° C. in the presence of 40% formamide, and washed with 2×SSC containing 0.1% SDS at 55° C.

Figure 13:
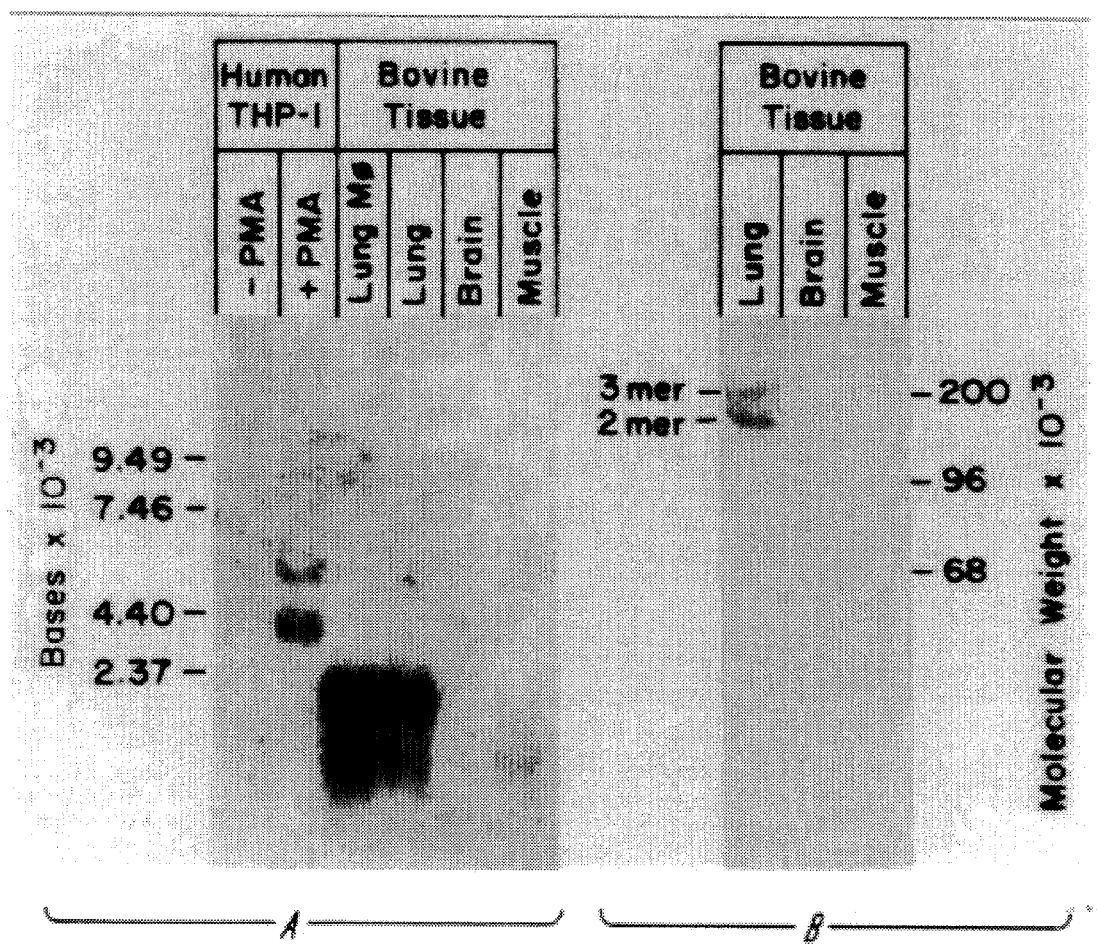
FIG. 13 is a photographic representation of an autoradiogram of a Northern blot using RNA isolated from various cell and tissue types and a DNA probe encoding the collagen domain.

The results are shown in FIG. 13(A). RNA sequences encoding the Col domain are detected in THP-1 PMA(+) (differentiated) macrophages as well as in alveolar macrophages and lung. This pattern of RNA expression is the same as the pattern of in vivo receptor expression.

To simultaneously determine the amount of receptor activity in the same tissue specimens, receptor protein was purified from these bovine tissues (5 g per organ). The tissue was homogenized, maleyl-BSA-affinity purified, and subjected to immunoblotting using monoclonal anti-bovine receptor antibody IgG-D1 as described previously (Kodama, ibid.).

The results of this immunoblotting analysis are shown in FIG. 12(B). Receptor was detected in lung, but not in brain or muscle, as expected from the Northern blot results described above.

It can be seen from the foregoing description and examples that a receptor protein having a high affinity for Ac-LDL can be isolated and purified to near homogeneity from various appropriate mammalian tissues. Monoclonal antibodies can be made to this receptor protein which can aid in its identification and further purification, and which are useful in methods of detecting cellular structures that contain the receptor protein such as atherosclerotic plaques. In addition, DNA clones can be prepared which encode at least a portion of the scavenger receptor protein, and that these clones have the same pattern of differential expression in various tissue types as does the native receptor. Furthermore, the expressed protein has scavenger receptor protein-like activity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A substantially pure receptor protein capable of binding acetylated low density lipoprotein, said protein found on the surface of macrophages and characterized by:

being formed by combining three isolated subunits, each having an apparent molecular weight on polyacrylamide gels of about 77,000 daltons, the protein when glycosylated having an apparent molecular weight on SDS-polyacrylamide gels of about 220,000 daltons, and having a capacity for acetylated low density lipoprotein of approximately 1.4 mg of Acetyl-LDL protein/mg receptor protein, wherein the subunits are encoded by a DNA sequence specifically hybridizing to the DNA sequence shown in FIGS. 3A, 3B and 3C or FIGS. 4A, 4B and 4C.

2. An isolated 77,000 dalton protein subunit of a receptor protein capable of binding acetylated low density lipoprotein, wherein three of the isolated subunits, each having an apparent molecular weight on polyacrylamide gels of about 77,000 daltons, form a protein on the surface of macrophages, which when glycosylated has an apparent molecular weight on SDS-polyacrylamide gels of about 220,000 daltons.

3. The protein subunit of claim 2 further characterized as a glycoprotein.

4. The protein subunit of claim 3 further comprising an asparagine-linked carbohydrate chain.

5. The receptor protein of claim 1 wherein each of said subunits comprises an asparagine-linked carbohydrate chain.

6. The receptor protein of claim 1 further characterized by the ability to bind a negatively charged macromolecule selected from the group consisting of polyvinylsulfate, maleyl-BSA, fucoidan, and purine polynucleotides, poly[I-C], poly[I] and poly[G].

7. The protein subunit of claim 2 chemically coupled to an inert support for use in an assay or in a purification process.

8. The protein subunit of claim 7 wherein said protein subunit is capable of binding oxidized low density lipoprotein.

9. An isolated DNA molecule encoding a substantially pure receptor protein capable of binding acetylated low density lipoprotein, said protein found on the surface of macrophages and formed by combining three isolated subunits, each having an apparent molecular weight on polyacrylamide gels of about 77,000 daltons, the protein when glycosylated having an apparent molecular weight on SDS-polyacrylamide gels of about 220,000 daltons.

10. An isolated DNA molecule encoding the protein subunit of claim 2.

11. The DNA molecule of claim 10 comprising the sequence shown in FIGS. 3A, 3B and 3C.

12. The DNA molecule of claim 10 comprising the sequence shown in FIGS. 4A, 4B, 4C, and 4D.

13. The receptor protein of claim 1 comprising the amino acid sequence shown in FIGS. 3A, 3B and 3C.

14. The receptor protein of claim 1 wherein the subunits comprise the amino acid sequence shown in FIGS. 4A, 4B, 4C, and 4D.

15. The receptor protein of claim 1 which is expressed in procaryotic or yeast cells.

16. A substantially pure receptor protein, wherein the protein is capable of binding acetylated low density lipoprotein when the protein is found on the surface of macrophages, and wherein the protein is characterized by being formed by combining three isolated subunits, each having an apparent molecular weight on polyacrylamide gels of about 77,000 daltons, the protein when glycosylated having an apparent molecular weight on SDS-polyacrylamide gels of about 220,000 daltons, and having a capacity for acetylated low density lipoprotein of approximately 1.4 mg of Acetyl-LDL protein/mg receptor protein, having at least one subunit not including the transmembrane and cytoplasmic region.

17. The receptor protein of claim 1 chemically coupled to an inert support.

* * * * *